US012296001B2

United States Patent
Muthumani et al.

(10) Patent No.: US 12,296,001 B2
(45) Date of Patent: May 13, 2025

(54) DNA VACCINE AGAINST CRIMEAN-CONGO HEMORRHAGIC FEVER VIRUS (CCHFV)

(71) Applicant: THE WISTAR INSTITUTE OF ANATOMY AND BIOLOGY, Philadelphia, PA (US)

(72) Inventors: Kar Muthumani, Cherry Hill, NJ (US); David Weiner, Merion, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 974 days.

(21) Appl. No.: 17/289,297

(22) PCT Filed: Nov. 1, 2019

(86) PCT No.: PCT/US2019/059360
§ 371 (c)(1),
(2) Date: Apr. 28, 2021

(87) PCT Pub. No.: WO2020/092880
PCT Pub. Date: May 7, 2020

(65) Prior Publication Data
US 2021/0401965 A1     Dec. 30, 2021

Related U.S. Application Data

(60) Provisional application No. 62/754,821, filed on Nov. 2, 2018.

(51) Int. Cl.
| | |
|---|---|
| *A61K 39/12* | (2006.01) |
| *A61K 9/00* | (2006.01) |
| *A61K 38/20* | (2006.01) |
| *A61K 39/00* | (2006.01) |
| *A61K 39/39* | (2006.01) |
| *A61P 31/14* | (2006.01) |
| *C12N 7/00* | (2006.01) |

(52) U.S. Cl.
CPC ............ *A61K 39/12* (2013.01); *A61K 9/0009* (2013.01); *A61K 38/20* (2013.01); *A61K 38/208* (2013.01); *A61K 38/2086* (2013.01); *A61K 39/39* (2013.01); *A61P 31/14* (2018.01); *C12N 7/00* (2013.01); *A61K 2039/53* (2013.01); *A61K 2039/54* (2013.01); *A61K 2039/55527* (2013.01); *A61K 2039/55538* (2013.01); *C12N 2760/12234* (2013.01); *C12N 2760/12271* (2013.01)

(58) Field of Classification Search
CPC ...... A61K 39/12; A61K 9/0009; A61K 38/20; A61K 38/208; A61K 38/2086; A61K 39/39; A61K 2039/53; A61K 2039/54; A61K 2039/55527; A61K 2039/55538; A61P 31/14; C12N 7/00; C12N 2760/12234; C12N 2760/12271
See application file for complete search history.

(56) References Cited

U.S. PATENT DOCUMENTS

| | | | | |
|---|---|---|---|---|
| 11,602,557 | B2 * | 3/2023 | Petsch | .................... C12N 15/67 |
| 2015/0306202 | A1 | 10/2015 | Bergeron | |
| 2015/0361141 | A1 | 12/2015 | Buttigieg | |
| 2018/0169218 | A1 | 6/2018 | Thess | |
| 2021/0030864 | A1 * | 2/2021 | Petsch | ..................... C12N 7/00 |

FOREIGN PATENT DOCUMENTS

| | | | | |
|---|---|---|---|---|
| WO | 2017109134 | | 6/2017 | |
| WO | WO-2019038332 A1 * | | 2/2019 | ............. A61K 39/12 |

OTHER PUBLICATIONS

Spik K, et al. Immunogenicity of combination DNA vaccines for Rift Valley fever virus, tick-borne encephalitis virus, Hantaan virus, and Crimean Congo hemorrhagic fever virus. Vaccine. May 22, 2006;24(21):4657-66. (Year: 2006).*

Garrison AR, et al. A DNA vaccine for Crimean-Congo hemorrhagic fever protects against disease and death in two lethal mouse models. PLoS Negl Trop Dis. PLoS Negl Trop Dis. Sep. 18, 2017;11(9):e0005908. (Year: 2017).*

Saksida A, Duh D, Wraber B, Dedushaj I, Ahmeti S, Avsic-Zupanc T. Interacting roles of immune mechanisms and viral load in the pathogenesis of crimean-congo hemorrhagic fever. Clin Vaccine Immunol. Jul. 2010;17(7):1086-93. (Year: 2010).*

Xia et al., "Transstadial Transmission and Long-term Association of Crimean-Congo Hemorrhagic Fever Virus in Ticks Shapes Genome Plasticity", Scientific Reports, (Oct. 24, 2016), vol. 6, No. 35819, pp. 1-12, XP055703074.

* cited by examiner

*Primary Examiner* — Nicole Kinsey White
*Assistant Examiner* — Samadhan Jaising Jadhao
(74) *Attorney, Agent, or Firm* — Riverside Law LLP

(57) ABSTRACT

Nucleic acid molecules and compositions comprising one or more nucleic acid sequences that encode a consensus Crimean-Congo hemorrhagic fever virus (CCHFV) antigens. Immunomodulatory methods and methods of inducing an immune response against CCHFV are disclosed. CCHFV glycoprotein immunogens are disclosed.

14 Claims, 7 Drawing Sheets

Specification includes a Sequence Listing.

| Peptide # | Position | Sequence info | |
|---|---|---|---|
| Peptide 1 | 19-37 | GNGLVDTFTNSYSFC | (SEQ ID NO:5) |
| Peptide 2 | 28-46 | DTFTNSYSFCESVPN | (SEQ ID NO:6) |
| Peptide 3 | 145-163 | TAALSNKVLAEYKVP | (SEQ ID NO:7) |
| Peptide 4 | 262-280 | DEVDRASADSMITNL | (SEQ ID NO:8) |
| Peptide 5 | 298-316 | AQIDTAFSSYYWLYK | (SEQ ID NO:9) |
| Peptide 6 | 343-361 | KMKKALLSTPMKWGK | (SEQ ID NO:10) |
| Peptide 7 | 397-415 | DDAAQGSGHTKSILN | (SEQ ID NO:11) |
| Peptide 8 | 442-460 | MDIVASEHLLHQSLV | (SEQ ID NO:12) |
| Peptide 9 | 451-469 | SEHLLHQSLVGKQSP | (SEQ ID NO:13) |
| Peptide 10 | 460-478 | SPFQNAYNVKGNATS | (SEQ ID NO:14) |

DNA VACCINE AGAINST CRIMEAN-CONGO HEMORRHAGIC FEVER VIRUS (CCHFV)

CROSS-REFERENCE TO RELATED APPLICATIONS

This application is a national phase application filed under 35 U.S.C. § 371 claiming benefit to PCT International Application PCT/US2019/059360, filed Nov. 1, 2019, which claims priority to U.S. Provisional Application No. 62/754,821, filed Nov. 2, 2018, the disclosures of which are hereby incorporated by reference herein in their entireties.

FIELD OF THE INVENTION

The present invention relates to vaccines for inducing immune responses and preventing Crimean-Congo hemorrhagic fever virus (CCHFV) infection and/or treating individuals infected with CCHFV. The present invention relates to consensus CCHFV proteins and nucleic acid molecules which encode the same.

BACKGROUND OF THE INVENTION

Crimean-Congo Haemorrhagic fever (CCHF) is a viral haemorrhagic fever caused by a virus of the Nairovirus group (CCHFV). CCHF is a zoonosis, and infects a range of domestic and wild animals. It is spread via the bite of an infected tick. CCHF was first described in the Crimea in 1944 among soldiers and agricultural workers, and in 1969 it was recognized that the virus causing the disease was identical to a virus isolated from a child in the Congo in 1956.

The causative organism is found in Asia, Eastern Europe, the Middle East, a belt across central Africa and South Africa and Madagascar. The main environmental reservoir and vector for the virus is hard ticks. Ticks carry the virus to domestic animal stock. Sheep, goats and cattle can develop viremia, but tend not to fall ill. Tick species that have been identified as infected with this virus include *Argas reflexus, Hyalomma anatolicum, Hyalomma detritum, Hyalomma marginatum* and *Rhipicephalus sanguineus*.

CCHFV is transmitted from infected human by contact with infectious blood or body fluids. The Incubation period is around 3-7 days. Hemorrhagic fever is around 3-6 days following clinical signs. The target organ is the vascular bed. Complications may include liver failure. Disseminated intravascular coagulation may occur, as well as acute kidney failure, shock, and sometimes acute respiratory distress syndrome. Fatality rates are around 50%.

CCHF is an emerging virus, whereby incidence and geographic range has been increasing since its early identification. CCHF viral load is an important factor for both the severity and outcome of disease-acknowledged in many studies. Levels of the chemokine CXCL10 (also known as IP-10) with CCHF viral load suggests that it is involved in pathogenesis. CCHFV has been listed as a potential agent of bioterrorism/biowarfare because of aerosol route infection. US-NIAID list the virus as a Category C priority pathogen. There are currently no approved therapies for CCHF, and supportive care is often the only option.

Therefore, there is need in the art for protective vaccines against CCHFV. The current invention satisfies this unmet need.

SUMMARY OF THE INVENTION

A composition comprising a nucleic acid sequence that encodes a synthetic consensus Crimean-Congo hemorrhagic fever virus (CCHFV) envelope glycoprotein immunogen is provided. The amino acid sequence of the synthetic consensus CCHFV envelope glycoprotein immunogen may be SEQ ID NO:2 or SEQ ID NO:4, a fragment of SEQ ID NO:2 or SEQ ID NO: 4, an amino acid sequence that is homologous to SEQ ID NO:2 or SEQ ID NO:4, or a fragment of an amino acid sequence that is homologous to SEQ ID NO:2 or SEQ ID NO:4. Amino acid sequences that are homologous to SEQ ID NO:2 or SEQ ID NO:4 are typically 95% or more, 96% or more, 97% or more, 99% or more, or 99% or more, homologous to SEQ ID NO: 2 or SEQ ID NO:4. Fragments of SEQ ID NO:2 or SEQ ID NO:4, or fragments of amino acid sequences that are homologous to SEQ ID NO:2 or SEQ ID NO:4 are typically 600 or more, 637 or more, or 670 or more amino acids.

A composition comprising a nucleic acid sequence that encodes a CCHFV envelope glycoprotein immunogen is also provided. The amino acid sequence of a CCHFV immunogen may be SEQ ID NO:2, a fragment of SEQ ID NO:2, an amino acid sequence that is homologous to SEQ ID NO:2, or a fragment of an amino acid sequence that is homologous to SEQ ID NO:2. Amino acid sequences that are homologous to SEQ ID NO:2 are typically 95% or more, 96% or more, 97% or more, 99% or more, or 99% or more, homologous to SEQ ID NO:2. Fragments of SEQ ID NO:2 or fragments of amino acid sequences that are homologous to SEQ ID NO:2 are typically 600 or more, 637 or more, or 670 or more amino acids. The amino acid sequence of a CCHFV envelope glycoprotein immunogen may be SEQ ID NO:4, a fragment of SEQ ID NO:4, an amino acid sequence that is homologous to SEQ ID NO:4, or a fragment of an amino acid sequence that is homologous to SEQ ID NO:4. Amino acid sequences that are homologous to SEQ ID NO:4 are typically 95% or more, 96% or more, 97% or more, 99% or more, or 99% or more, homologous to SEQ ID NO:4. Fragments of SEQ ID NO:4 or fragments of amino acid sequences that are homologous to SEQ ID NO:4 are typically 600 or more, 637 or more, or 670 or more amino acids.

The nucleic acid sequence encoding the consensus CCHFV envelope glycoprotein immunogen may be SEQ ID NO:1 or SEQ ID NO:3, or a fragment of SEQ ID NO:1 or SEQ ID NO: 3, or a fragment of a nucleic acid sequence that is homologous to SEQ ID NO:1 or SEQ ID NO: 3. Nucleic acid sequences that are homologous to SEQ ID NO: 1 or SEQ ID NO:3 are typically 95% or more, 96% or more, 97% or more, 99% or more, or 99% or more, homologous to SEQ ID NO:1 or SEQ ID NO:3. Fragments of SEQ ID NO:1 or SEQ ID NO:3 that are homologous to SEQ ID NO:1 or SEQ ID NO:3 are typically 1800 or more, 1890 or more, or 1980 or more nucleotides.

Each of the different nucleic acid sequences may be on a single nucleic acid molecule, may each be on a separate nucleic acid molecules or various permutations. Nucleic acid molecules may be plasmids.

The composition may be formulated for delivery to an individual using electroporation.

The composition may further comprise nucleic acid sequences that encode one or more proteins selected from the group consisting of: IL-12, IL-15 and IL-28.

The composition may be used in methods of inducing an immune response against CCHFV.

Methods of treating an individual who has been diagnosed with CCHFV comprising administering a therapeutically effective amount of the composition to an individual are provided.

Method of preventing CCHFV infection in an individual are provided. The methods comprise administering a prophylactically effective amount of the composition to an individual.

BRIEF DESCRIPTION OF THE DRAWINGS

Figure 1A:
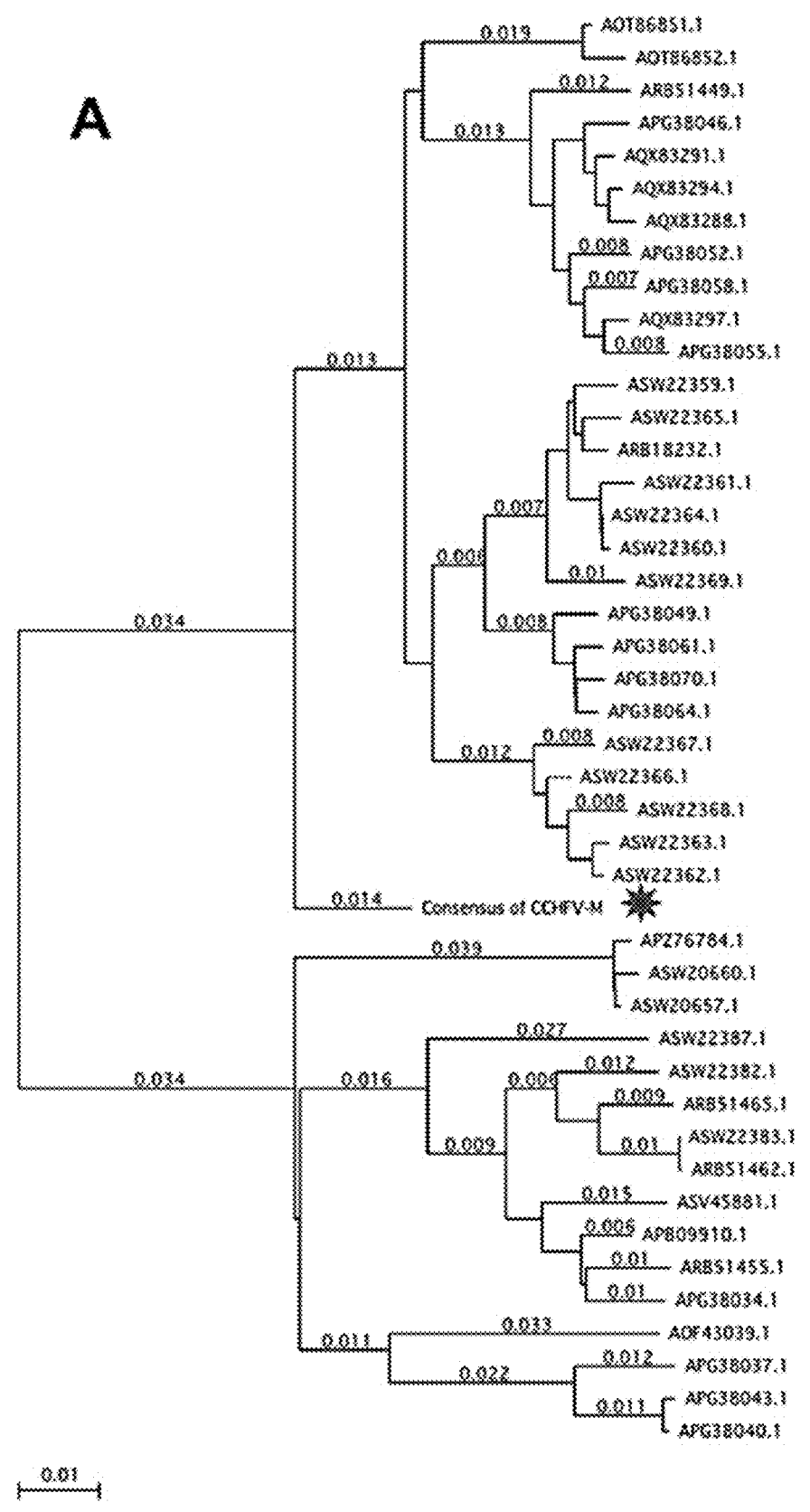

FIG. 1A through FIG. 1C depict the design for CCHFV-consensus immunogens. FIG. 1A depicts a phylogenic analysis based on neighbor joining evaluation of CCHFV-M-sequences deposited in GenBank. The position of the CCHFV-M vaccine sequence in this tree is noted with an asterisk "*". FIG. 1B depicts a schematic of the CCHFV-M vaccine construct generated and cloned into expression vector pMV101. FIG. 1C depicts an agarose gel photograph showing the CCHFV plasmid indicated digested with BamH1 and Xho1 double digestion.

FIG. 2A and FIG. 2B depict the design for CCHFV-Glycoprotein-IBAr10200 strain. FIG. 2A depicts a schematic of the CCHFV-IBAr10200 matched strain vaccine construct generated and cloned into expression vector pMV101. FIG. 2B depicts an agarose gel photograph showing the CCHFV plasmid indicated digested with BamH1 and Xho1 double digestion.

FIG. 3A through FIG. 3D depict exemplary experiments demonstrating that CCHFV-vaccine induces humoral response in mice. FIG. 3A depicts a schematic representation of C57BL/6 mice immunized with CCHFV vaccine. FIG. 3B and FIG. 3C depict the results of an ELISA of sera from CCHFV-immunized mice. C57BL/6 mice (n=4) were immunized three times using EP-enhanced i.m. injection with 25 μg of CCHFV-Consensus, CCHFV-IBAr10200 strain or pMV101 empty vector plasmid at 2-week intervals with sera collected one week after each immunization. Immune sera from mice were evaluated for their binding capacity to total cell lysates protein. Day 35 pooled, immune sera were diluted to 1:50 or 1:1. Serum was collected and subjected to analysis for total IgG production. Serum was incubated for 1 hour at 37° C. on 96-well plates coated with CCHFV-cell lysates and antibody production was detected using anti-mouse IgG-HRP. Values represent the mean (±S.D.) of triplicate wells. FIG. 3D depicts a western blot analysis of CCHFV-vaccine immunized murine sera. Pooled day 35 sera were used as a primary antibody to probe CCHFV-glycoproteins and pMV101-transfected 293T cell lysates as a negative control.

FIG. 4 depicts an indirect immunofluorescence assay. Characterization of CCHFV-M vaccine induced immune sera by immunofluorescence assay (IFA). Indirect immunofluorescence assay of MAYV-infected Vero cells incubated with pooled day 35 sera from pMV101 or CCHFV-vaccine immunized mice followed by FITC-tagged anti-mouse IgG secondary antibody (green) and DAPI (blue) to identify nuclei. An immunofluorescence assay demonstrated that IgG generated from CCHFV-M administered mice was capable of binding to CCHFV-M vaccine transfected Vero cells.

FIG. 5A and FIG. 5B depict the CCHFV-M antigen specific cellular immune response in mice. Interferon-γ response to CCHFV-M protein measured by ELISpot. C57BL/6 mice were immunized three times, each 2 weeks apart, with 25 μg pMV101 vector or CCHFV-con or CCHFV-IBAr10200 matched strain as indicated and sacrificed 1 week later (day 35). Splenocytes were harvested and cultured overnight in the presence of R10 (negative control) or 10 μg/ml of 10 different dominant peptide pools as published previously made up of 15-mer peptides, spanning the CCHFV-M protein (FIG. 5A). Average IFN-γ SFUs generated per $10^6$ splenocytes+/−SEM for each peptide pools are shown (FIG. 5B). SFU were quantified by an automated ELISpot reader, and the raw values were normalized to SFU per million splenocytes. Values represent the mean of triplicate wells.

DETAILED DESCRIPTION

Figures 1B, 1C:
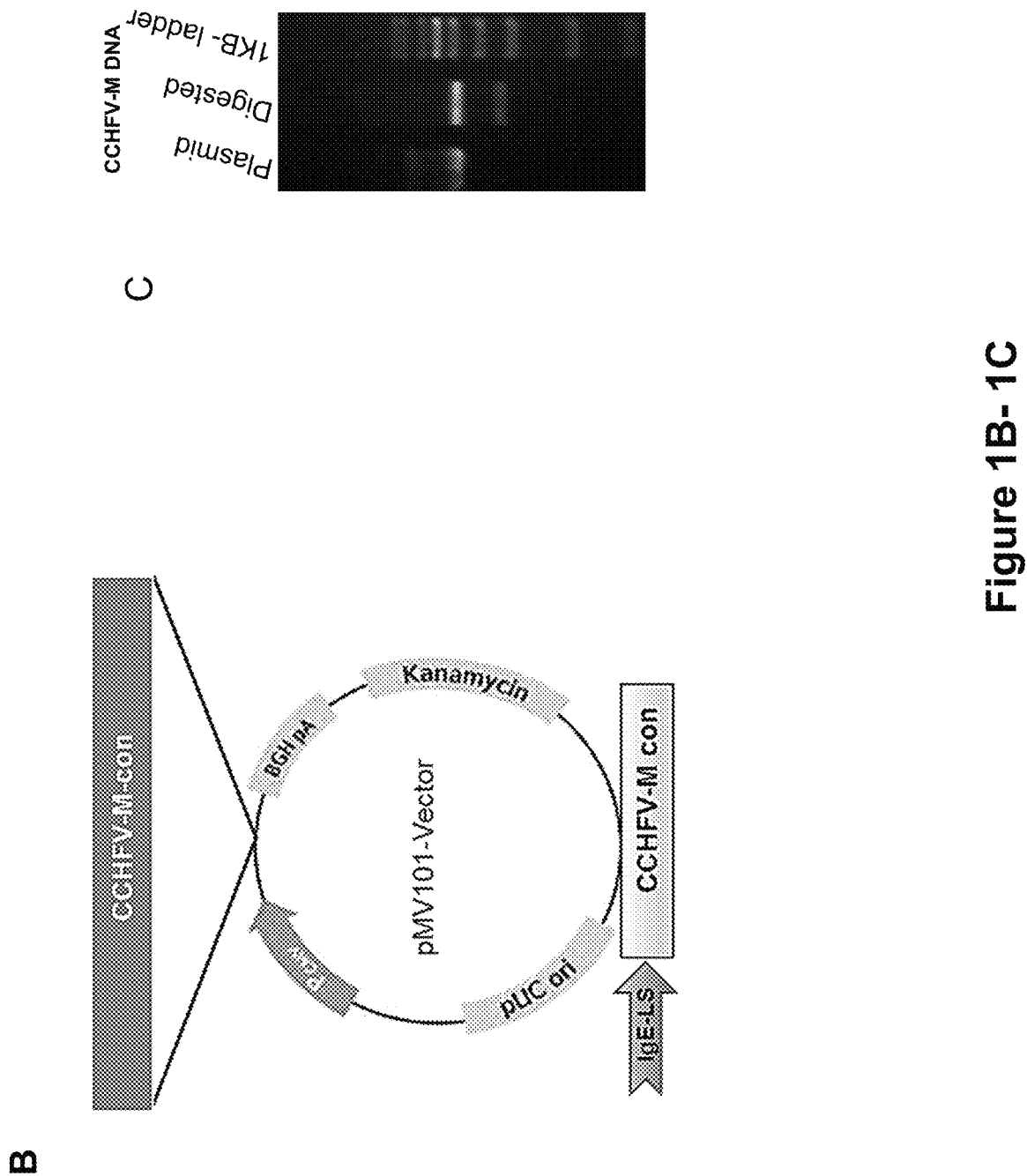

An aspect of the present invention provides an immunogenic composition comprising one or more nucleic acid molecules comprising one or more nucleic acid sequences capable of generating in a mammal an immune response against Crimean-Congo hemorrhagic fever virus (CCHFV). In one embodiment, the nucleic acid molecules comprise one or more nucleic acid sequences capable of expressing a consensus CCHFV antigen in the mammal and a pharmaceutically acceptable excipient. In one embodiment, the nucleic acid molecule comprises a promoter operably linked to a coding sequence that encodes the consensus CCHFV antigen. In one embodiment, the consensus CCHFV antigen comprises consensus envelope glycoprotein (M). In one embodiment, the nucleic acid molecule comprises an optimized nucleic acid sequence encoding a consensus CCHFV antigen comprising an amino acid sequence at least 90% homologous to SEQ ID NO: 2 or at least 90% homologous to SEQ ID NO: 4.

In one embodiment, the present invention relates to a composition comprising a recombinant nucleic acid sequence that encodes consensus CCHFV antigen and functional fragments thereof. The composition can be administered to a subject in need thereof to elicit an immune response in the subject against CCHFV.

In one embodiment, the composition comprises one or more nucleotide sequences capable of expressing a consensus CCHFV antigen in the subject and a pharmaceutically acceptable excipient. In one embodiment, the nucleic acid molecule comprises a promoter operably linked to a coding sequence that encodes the consensus CCHFV antigen.

In one embodiment, the invention includes a nucleic acid vaccine against CCHFV. As a vaccine candidate, an enhanced DNA (DNA)-based platform provides many advantages in genetic optimization and delivery techniques. As such, each CCHFV antigen can be genetically-optimized, subcloned into modified mammalian expression vectors, and then delivered using in vivo electroporation (EP).

Vaccination in preclinical rodent studies was highly potent, as vaccination with synthetic consensus CCHFV antigen constructs generates robust immune responses.

In various embodiments, the invention provides coding sequences for optimized and consensus CCHFV antigens.

Optimization of plasmid DNA vectors and their encoded antigen genes have led to increases in in vivo immunogenicity. Cellular uptake and subsequent antigen expression are substantially amplified when highly-concentrated plasmid vaccine formulations are administered with in vivo electroporation, a technology that uses brief square-wave electric pulses within the vaccination site to drive plasmids into transiently permeabilized cells. Immunity can be further directed by co-delivery with plasmid molecular adjuvants encoding species-specific cytokine genes as well as 'consensus-engineering' of the antigen amino acid sequences to help bias vaccine-induced immunity towards particular strains.

Definitions:

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein may mean any molecule added to a nucleic acid vaccines to enhance antigenicity of the vaccine.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes an antibody as set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Consensus" or "consensus sequence" as used herein may mean a synthetic nucleotide sequence, or corresponding polypeptide sequence, constructed based on analysis of an alignment of multiple sequences (e.g., multiple sequences of a particular virus antigen.)

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a percentage of a full length polypeptide sequence or nucleotide sequence. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the full length of the parental nucleotide sequence or amino acid sequence or variant thereof.

"Genetic construct" as used herein refers to the DNA or RNA molecules that comprise a nucleotide sequence which encodes a protein, such as an antibody. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Description

The invention is based, in part on the development of an optimized consensus sequence encoding a Crimean-Congo hemorrhagic fever virus (CCHFV) antigen. In one embodiment, the CCHFV antigen is encoded by optimized consensus sequences.

Provided herein are CCHFV consensus antigens that can be used to induce broad immunity against CCHFV. In some embodiments, the antigens may comprise a signal peptide from a different protein such as an immunoglobulin protein, for example an IgE signal peptide or an IgG signal peptide.

Vaccine

The invention provides an optimized sequence encoding a CCHFV antigen. In one embodiment, the CCHFV antigen encoded by the optimized sequence is capable of eliciting an immune response in a mammal. In one embodiment, the CCHFV antigen encoded by the optimized sequence can comprise an epitope(s) that makes it particularly effective as an immunogen against which an immune response can be induced.

In one embodiment, the optimized consensus sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The CCHFV antigen encoded by the optimized sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized sequence can comprise a hemagglutinin (HA) tag. The antigen encoded by the optimized sequence can be designed to elicit stronger cellular and/or humoral immune responses than a corresponding non-optimized antigen.

Provided herein are CCHFV antigens that can be used to induce immunity against CCHFV in subjects susceptible to CCHFV infection. In one embodiment, the present invention provides an immunogenic composition comprising one or more nucleic acid molecules that are capable of generating in a mammal an immune response against a CCHFV antigen. The present invention also provides isolated nucleic acid molecules that are capable of generating in a mammal an immune response against a CCHFV antigen. In one embodiment, the nucleic acid molecule comprises an optimized nucleotide sequence encoding the CCHFV antigen. In one embodiment, the CCHFV antigen is a consensus CCHFV antigen.

In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α).

The vaccine can increase a cellular immune response in a subject administered the vaccine by about 2-fold to about 6000-fold, about 3-fold to about 6000-fold, about 4-fold to about 6000-fold, about 5-fold to about 6000-fold, about 6-fold to about 6000-fold, about 7-fold to about 6000-fold, about 8-fold to about 6000-fold, about 9-fold to about 6000-fold, about 10-fold to about 6000-fold, about 15-fold to about 6000-fold, about 10-fold to about 6000-fold, about 25-fold to about 6000-fold, about 30-fold to about 6000-fold, about 35-fold to about 6000-fold, about 40-fold to about 6000-fold, about 45-fold to about 6000-fold, about 50-fold to about 6000-fold, about 2-fold to about 5500-fold, about 2-fold to about 5000-fold, about 2-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments the vaccine can increase the cellular immune response in the subject administered the vaccine by about 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the vaccine.

The vaccine can increase interferon gamma (IFN-γ) levels in a subject administered the vaccine by about 2-fold to about 6000-fold, about 3-fold to about 6000-fold, about 4-fold to about 6000-fold, about 5-fold to about 6000-fold, about 6-fold to about 6000-fold, about 7-fold to about 6000-fold, about 8-fold to about 6000-fold, about 9-fold to about 6000-fold, about 10-fold to about 6000-fold, about 15-fold to about 6000-fold, about 10-fold to about 6000-fold, about 25-fold to about 6000-fold, about 30-fold to about 6000-fold, about 35-fold to about 6000-fold, about 40-fold to about 6000-fold, about 45-fold to about 6000-fold, 50-fold to about 6000-fold, about 2-fold to about 5500-fold, about 2-fold to about 5000-fold, about 2-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the vaccine. In some embodiments the vaccine can increase IFN-γ levels in the subject administered the vaccine by about 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the vaccine.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the one or more CCHFV antigens. The RNA vaccine can be introduced into the cell.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing neutralizing antibody; inducing protective T cell responses; and providing case of administration, few side effects, biological stability, and low cost per dose. The vaccine can accomplish some or all of these features by comprising the CCHFV antigen of the invention.

The synthetic consensus antigen can be a nucleic acid sequence, an amino acid sequence, or a combination thereof. The at least one CCHFV antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof. The CCHFV antigen can be a recombinant CCHFV antigen.

One manner for designing the nucleic acid and its encoded amino acid sequence of the CCHFV antigen is by creating an optimized consensus CCHFV antigen that has at least 85% and up to 99% amino acid sequence identity to its corresponding native CCHFV antigen; at least 90% and up to 98% sequence identity; at least 93% and up to 98% sequence identity; or at least 95% and up to 98% sequence identity. In some embodiments, the optimized consensus CCHFV antigen has 95%, 96%, 97%, 98%, or 99% amino acid sequence identity to its corresponding native CCHFV antigen. The native CCHFV antigen is the antigen normally associated with CCHFV. Depending upon the CCHFV antigen, the consensus sequence of the CCHFV antigen can be across viral strains or serotypes.

CCHFV Antigen

The vaccine of the present invention can comprise at least one synthetic consensus CCHFV antigen, a fragment thereof, or a variant thereof.

The nucleic acid sequence encoding the CCHFV antigen or consensus CCHFV antigen can be optimized with regards to codon usage and corresponding RNA transcripts. The nucleic acid encoding the CCHFV antigen or consensus CCHFV antigen can be codon and RNA optimized for expression in mammals. In some embodiments, the nucleic acid sequence encoding the CCHFV antigen or consensus CCHFV antigen can include a Kozak sequence to increase the efficiency of translation. The nucleic acid encoding the CCHFV antigen or consensus CCHFV antigen can include or be operably linked to one or multiple stop codons (e.g., encoded by a sequence such as TGA or TGATAA) to increase the efficiency of translation termination.

The nucleic acid encoding the CCHFV antigen or consensus CCHFV antigen can also encode an immunoglobulin E (IgE) leader sequence. The nucleic acid encoding the CCHFV antigen or consensus CCHFV antigen can further encode the IgE leader sequence such that the amino acid sequence of the IgE leader sequence is linked to the amino acid sequence of the CCHFV antigen or consensus CCHFV antigen by a peptide bond, respectively. In some embodiments, the nucleic acid encoding the CCHFV antigen or consensus CCHFV antigen is free of or does not contain a nucleotide sequence encoding the IgE leader sequence.

Consensus amino acid sequences for CCHFV antigens include SEQ ID NO:2, SEQ ID NO: 4, and variants thereof and fragments of SEQ ID NO:2, SEQ ID NO:4 and variants thereof.

In one embodiment, the invention provides compositions comprising a nucleic acid molecule comprising a nucleotide sequence that encodes a synthetic consensus CCHFV antigen. In one embodiment, a nucleotide sequence which encodes a synthetic consensus CCHFV antigen is provided as SEQ ID NO:1, which encodes SEQ ID NO:2. In one embodiment, a nucleotide sequence which encodes a synthetic consensus CCHFV antigen is provided as SEQ ID NO:3, which encodes SEQ ID NO:4.

Compositions may comprise a single nucleic acid molecule, such as a plasmid, that contains coding sequence for multiple consensus CCHFV antigens. In one embodiment, each coding sequence for each consensus CCHFV antigen is on a separate plasmid.

In some embodiments, the sequence can be the nucleotide sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO:1 or SEQ ID NO:3. In other embodiments, sequence can be the nucleotide sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2 or SEQ ID NO: 4.

In some embodiments, the nucleic acid molecule comprises an RNA sequence that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO:1 or SEQ ID NO:3. In some embodiments, the nucleic acid molecule comprises an RNA sequence that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the amino acid sequence set forth in SEQ ID NO:2 or SEQ ID NO:4.

The optimized CCHFV antigen can be a peptide having the amino acid sequence set forth in SEQ ID NO:2 or SEQ ID NO:4. In some embodiments, the antigen can have an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2 or SEQ ID NO:4.

Immunogenic fragments of SEQ ID NO:2 or SEQ ID NO:4 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of the full length of SEQ ID NO:2 or SEQ ID NO:4. In some embodiments, immunogenic fragments are free of a leader sequence.

Immunogenic fragments of proteins with amino acid sequences homologous to immunogenic fragments of SEQ ID NO:2 or SEQ ID NO:4 can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2 or SEQ ID NO:4. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

In one embodiment, an immunogenic fragment of a nucleic acid molecule encodes at least one immunodominant or sub-immunodominant epitope of a full length optimized consensus CCHFV antigen.

In one embodiment, the nucleic acid molecule comprises a sequence at least 90% homologous to SEQ ID NO:1 or SEQ ID NO:3.

In some embodiments, the nucleic acid molecule includes a sequence that encodes for a CCHFV antigen minus an IgE leader sequence on the N-terminal end of the coding sequence. In some embodiments, the DNA nucleic acid molecule further comprises an IgE leader sequence attached to an N-terminal end of the coding sequence and operably linked to the promoter.

The nucleic acid molecule can further include a polyadenylation sequence attached to the C-terminal end of the coding sequence. In one embodiment, the nucleic acid molecule is codon optimized.

In some embodiments, the CCHFV antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:1 or SEQ ID NO:3. In some embodiments, the CCHFV antigen can be an RNA encoded by a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO: 1 or SEQ ID NO:3. In some embodiments, the CCHFV antigen can be an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2 or SEQ ID NO:4. In other embodiments, the CCHFV antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in one of SEQ ID NO:2 or SEQ ID NO:4. The CCHFV antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2 or SEQ ID NO:4.

Some embodiments relate to fragments of SEQ ID NO:1, SEQ ID NO:2, SEQ ID NO:3 or SEQ ID NO:4. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:1, SEQ ID NO:2, SEQ ID NO:3 or SEQ ID NO:4. Fragments can be at least 95%, at least 96%, at least 97%, at least 98%, or at least 99% homologous to fragments of SEQ ID NO:1, SEQ ID NO:2, SEQ ID NO:3 or SEQ ID NO: 4. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:1, SEQ ID NO:2, SEQ ID NO:3 or SEQ ID NO:4. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Fragments of SEQ ID NO: 1 or SEQ ID NO:3 may comprise at least 30, 45, 60, 75, 90, 120, 150, 180, 210, 240, 270, 300, 360, 420, 480, 540, 600, 660, 720, 780, 840, 900, 960, 1020, 1080, 1140, 1200, 1260, 1320, 1380, 1440, 1500, 1560, or more nucleotides of SEQ ID NO:1 or SEQ ID NO:3. In one embodiment, fragments of SEQ ID NO:1 or SEQ ID NO:3 comprise sequences that encode an immunodominant epitope.

Fragments of SEQ ID NO:1 or SEQ ID NO:3 may comprise fewer than 60, 75, 90, 120, 150, 180, 210, 240, 270, 300, 360, 420, 480, 540, 600, 660, 720, 780, 840, 900, 960, 1020, 1080, 1140, 1200, 1260, 1320, 1380, 1440, 1500, 1560, or fewer than 1560 nucleotides of SEQ ID NO: 1 or SEQ ID NO:3.

Fragments of SEQ ID NO:2 or SEQ ID NO:4 may comprise at least 15, 18, 21, 24, 30, 36, 42, 48, 54, 60, 72, 90, 120, 150, 180, 210, 240, 270, 300, 330, 360, 390, 420, 450, 480, 510, or more amino acids of SEQ ID NO:2 or SEQ ID NO:4. In some embodiments, fragments of SEQ ID NO:2 or SEQ ID NO:4 comprise an immunodominant epitope.

Fragments of SEQ ID NO:2 or SEQ ID NO:4 may comprise fewer than 24, 30, 36, 42, 48, 54, 60, 72, 90, 120, 150, 180, 210, 240, 270, 300, 330, 360, 390, 420, 450, 480, 510, or fewer than 1110 amino acids of SEQ ID NO:2 or SEQ ID NO:4.

Vaccine Constructs and Plasmids

The vaccine can comprise nucleic acid constructs or plasmids that encode the above described antigens. The nucleic acid constructs or plasmids can include or contain one or more heterologous nucleic acid sequences. Provided herein are genetic constructs that can comprise a nucleic acid sequence that encodes the above described antigens. The genetic construct can be present in the cell as a functioning extrachromosomal molecule. The genetic construct can be a linear minichromosome including centromere, telomeres or plasmids or cosmids. The genetic constructs can include or contain one or more heterologous nucleic acid sequences.

The genetic constructs can be in the form of plasmids expressing the above described antigens in any order.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer an initiation codon, a stop codon, or a polyadenylation signal.

The nucleic acid sequences can make up a genetic construct that can be a vector. The vector can be capable of expressing the above described antigens in the cell of a mammal in a quantity effective to elicit an immune response in the mammal. The vector can be recombinant. The vector can comprise heterologous nucleic acid encoding the above described antigens. The vector can be a plasmid. The vector can be useful for transfecting cells with nucleic acid encoding the above described antigens, which the transformed host cell is cultured and maintained under conditions wherein expression of the above described antigens takes place.

Coding sequences can be optimized for stability and high levels of expression. In some instances, codons are selected to reduce secondary structure formation of the RNA such as that formed due to intramolecular bonding.

The vector can comprise heterologous nucleic acid encoding the above described antigens and can further comprise an initiation codon, which can be upstream of the one or more CCHFV antigen coding sequence(s), and a stop codon, which can be downstream of the coding sequence(s) of the above described antigens. The initiation and termination codon can be in frame with the coding sequence(s) of the above described antigens. The vector can also comprise a promoter that is operably linked to the coding sequence(s) of the above described antigens. The promoter operably linked to the coding sequence(s) of the above described antigens can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the coding sequence(s) of the above described antigens. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, CA).

The vector can also comprise an enhancer upstream of the above described antigens. The enhancer can be necessary for DNA expression. The enhancer can be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, CA), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad CA). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

The backbone of the vector can be pAV0242. The vector can be a replication defective adenovirus type 5 (Ad5) vector.

The vector can also comprise a regulatory sequence, which can be well suited for gene expression in a mammalian cell into which the vector is administered. The one or more CCHFV antigen sequences disclosed herein can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells, such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

Immunogenic and Pharmaceutical Compositions

Immunogenic compositions, such as vaccines, are provided comprising an optimized CCHFV sequence, an optimized consensus CCHFV antigen, a fragment thereof, a variant thereof, or a combination thereof. The immunogenic composition can significantly induce an immune response of a subject administered with the immunogenic composition against the CCHFV antigen. The vaccine may comprise a plurality of the nucleic acid molecules, or combinations thereof. The vaccine may be provided to induce a therapeutic or prophylactic immune response.

Provided herein is an immunogenic composition capable of generating in a mammal an immune response against CCHFV. The immunogenic composition may comprise each plasmid as discussed above. The immunogenic composition may comprise a plurality of the plasmids, or combinations thereof. The immunogenic composition may be provided to induce a therapeutic or prophylactic immune response.

Immunogenic compositions may be used to deliver nucleic acid molecules that encode one or more optimized CCHFV antigen. Immunogenic compositions are preferably compositions comprising plasmids.

The immunogenic composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the immunogenic composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the immunogenic compositions may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the immunogenic composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the immunogenic composition. The one or more adjuvants may be proteins and/or nucleic acid molecules that encode proteins selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or a combination thereof.

In some embodiments, the adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/US10/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. Application Ser. No. and Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

The immunogenic composition may further comprise a genetic vaccine facilitator agent as described in U.S. Ser. No. 021,579 filed Apr. 1, 1994, which is fully incorporated by reference.

The immunogenic composition may comprise the CCHFV antigens or plasmids encoding the same at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the CCHFV antigen or plasmid thereof.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of a nucleic acid molecule of the invention. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of a nucleic acid molecule of the invention. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of a nucleic acid molecule of the invention.

In other embodiments, the pharmaceutical composition can comprise up to and including 15, 20, 25, 30, 35, 40, 45, 50, 55, 60, 65, 70, 75, 80, 85, 90, 95 or 100 nanograms of a nucleic acid molecule of the invention. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of a nucleic acid molecule of the invention. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of a nucleic acid molecule of the invention.

The immunogenic composition may be formulated according to the mode of administration to be used. An injectable immunogenic composition pharmaceutical composition may be sterile, pyrogen free and particulate free. An isotonic formulation or solution may be used. Additives for isotonicity may include sodium chloride, dextrose, mannitol, sorbitol, and lactose. The immunogenic composition may comprise a vasoconstriction agent. The isotonic solutions may include phosphate buffered saline. Immunogenic composition may further comprise stabilizers including gelatin and albumin. The stabilizing may allow the formulation to be stable at room or ambient temperature for extended periods of time such as LGS or polycations or polyanions to the immunogenic composition formulation.

The immunogenic composition may be stable at room temperature (25° C.) for more than 1 week, in some embodiments for more than 2 weeks, in some embodiments for more than 3 weeks, in some embodiments for more than 4 weeks, in some embodiments for more than 5 weeks, and in some embodiments for more than 6 weeks. In some embodiments, the vaccine is stable for more than one month, more than 2 months, more than 3 months, more than 4 months, more than 5 months, more than 6 months, more than 7 months, more than 8 months, more than 9 months, more than 10 months, more than 11 months, or more than 12 months. In some embodiments, the vaccine is stable for more than 1 year, more than 2 years, more than years, or more than 5 years. In one embodiment, the immunogenic composition is stable under refrigeration (2-8° C.). Accordingly, in one embodiment, the immunogenic composition does not require frozen cold-chain. An immunogenic composition is stable if it retains its biological activity for a sufficient period to allow its intended use (e.g., to generate an immune response in a subject). For example, for immunogenic compositions that are to be stored, shipped, etc., it may be desired that the immunogenic compositions remain stable for months to years.

Immune Response

The immunogenic composition can induce a humoral immune response in the subject administered the immunogenic composition. The induced humoral immune response can be specific for a CCHFV antigen. The induced humoral immune response can be reactive with the CCHFV antigen related to the optimized CCHFV antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized CCHFV antigen.

The humoral immune response induced by the immunogenic composition can include an increased level of IgG antibodies associated with the subject administered the immunogenic composition as compared to a subject not administered the immunogenic composition. These IgG antibodies can be specific for the CCHFV antigen genetically related to the optimized CCHFV antigen. These IgG antibodies can be reactive with the CCHFV antigen genetically related to the optimized CCHFV antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized CCHFV antigen.

The immunogenic composition can induce a cellular immune response in the subject administered the immunogenic composition. The induced cellular immune response can be specific for a CCHFV antigen related to the optimized CCHFV antigen. The induced cellular immune response can be reactive to a CCHFV antigen related to the optimized CCHFV antigen. The induced cellular immune response can include eliciting a CD8+ T cell response. The elicited CD8+ T cell response can be reactive with a CCHFV antigen genetically related to the optimized CCHFV antigen. The elicited CD8+ T cell response can be polyfunctional. The induced cellular immune response can include eliciting a CD8+ T cell response, in which the CD8+ T cells produce interferon-gamma (IFN-γ), tumor necrosis factor alpha (TNF-α), interleukin-2 (IL-2), or a combination of IFN-γ and TNF-α.

The induced cellular immune response can include an increased CD8+ T cell response associated with the subject administered the immunogenic composition as compared to the subject not administered the immunogenic composition. The CD8+ T cell response associated with the subject administered the immunogenic composition can be increased by about 2-fold to about 30-fold, about 3-fold to about 25-fold, or about 4-fold to about 20-fold as compared to the subject not administered the immunogenic composition. The CD8+ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition or a subject administered a non-optimized CCHFV antigen.

The induced cellular immune response can include an increased frequency of CD107a/IFNγ/T-bet triple-positive CD8 T cells that are reactive against the CCHFV antigen. The frequency of CD107a/IFNγ/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized CCHFV antigen.

The induced cellular immune response can include an increased frequency of CD107a/IFNγ double-positive CD8 T cells that are reactive against the CCHFV antigen. The frequency of CD107a/IFNγ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition or a subject administered a non-optimized CCHFV antigen.

The cellular immune response induced by the immunogenic composition can include eliciting a CD4+ T cell response. The elicited CD4+ T cell response can be reactive with a CCHFV antigen genetically related to the optimized CCHFV antigen. The elicited CD4+ T cell response can be polyfunctional. The induced cellular immune response can include eliciting a CD4+ T cell response, in which the CD4+ T cells produce IFN-γ, TNF-α, IL-2, or a combination of IFN-γ and TNF-α.

The induced cellular immune response can include an increased frequency of CD4+ T cells that produce IFN-γ. The frequency of CD4+IFN-γ+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized CCHFV antigen.

The induced cellular immune response can include an increased frequency of CD4+ T cells that produce TNF-α. The frequency of CD4+ TNF-α+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition or a subject administered a non-optimized CCHFV antigen.

The induced cellular immune response can include an increased frequency of CD4+ T cells that produce both IFN-γ and TNF-α. The frequency of CD4+IFN-γ+TNF-α+ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition or a subject administered a non-optimized CCHFV antigen.

The immunogenic composition can further induce an immune response when administered to different tissues such as the muscle or skin. The immunogenic composition can further induce an immune response when administered via electroporation, or injection, or subcutaneously, or intramuscularly.

Vector

The nucleotide construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid construct may be chimeric, meaning that at least one of its components is heterologous with respect to at least one of its other components.

Plasmid

The one or more vectors can be a plasmid. The plasmid may be useful for transfecting cells with the recombinant nucleic acid construct. The plasmid may be useful for introducing the recombinant nucleic acid construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in Escherichia coli (E. coli). The plasmid may also be pYES2 (Invitrogen, San Diego, Calif.), which may be used for protein production in Saccharomyces cerevisiae strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NO: 1 or SEQ ID NO:3, or a variant thereof or a fragment thereof. In another embodiment, the nucleotide sequence comprises an RNA sequence transcribed by a DNA sequence encoding a polypeptide sequence at least 90% homologous to one of SEQ ID NO:2 or SEQ ID NO:4 or a variant thereof or a fragment thereof. Accordingly, in one embodiment, the invention provides an RNA molecule encoding one or more of the CCHFV antigens. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid construct. The LEC may be any linear DNA devoid of any phosphate backbone. The LEC may not contain any antibiotic resistance genes and/or a phosphate backbone. The LEC may not contain other nucleotide sequences unrelated to the desired gene expression.

The LEC may be derived from any plasmid capable of being linearized. The plasmid may be capable of expressing the heavy chain polypeptide and/or light chain polypeptide encoded by the recombinant nucleic acid construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid construct.

The LEC can be pcrM2. The LEC can be pcrNP. pcrNP and pcrMR can be derived from pNP (Puerto Rico/34) and pM2 (New Caledonia/99), respectively.

Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Method of Preparing the Vector

Provided herein is a method for preparing the one or more vectors in which the recombinant nucleic acid construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

Methods

Provided herein are methods of treating, protecting against, and/or preventing a CCHFV associated disease in a subject in need thereof by administering one or more immunogenic composition described herein to the subject. Administration of the immunogenic composition to the subject can induce or elicit an immune response in the subject. The induced immune response can be used to treat, prevent, and/or protect against disease, for example, CCHFV infection or a disease or disorder associated with CCHFV infection.

Provided herein is a method for delivering the immunogenic composition for providing genetic constructs and proteins of the CCHFV antigen which comprise epitopes that make them particular effective against CCHFV, against which an immune response can be induced. The method of delivering the immunogenic composition or vaccination may be provided to induce a therapeutic and prophylactic immune response. The vaccination process may generate in the mammal an immune response against CCHFV. The immunogenic composition may be delivered to an individual to modulate the activity of the mammal's immune system and enhance the immune response. The delivery of the immunogenic composition may be the transfection of the CCHFV antigen as a nucleic acid molecule that is expressed in the cell and delivered to the surface of the cell upon which the immune system recognized and induces a cellular, humoral, or cellular and humoral response. The delivery of the immunogenic composition may be used to induce or elicit and immune response in mammals against CCHFV by administering to the mammals the immunogenic composition as discussed above.

Upon delivery of the immunogenic composition and plasmid into the cells of the mammal, the transfected cells will express and secrete CCHFV antigens for each of the plasmids injected from the immunogenic composition. These proteins will be recognized as foreign by the immune system and antibodies will be made against them. These antibodies will be maintained by the immune system and allow for an effective response to subsequent infections by CCHFV.

The induced immune response can include an induced humoral immune response and/or an induced cellular immune response. The humoral immune response can be induced by about 1.5-fold to about 16-fold, about 2-fold to about 12-fold, or about 3-fold to about 10-fold. The induced cellular immune response can include a CD8+ T cell response, which is induced by about 2-fold to about 30-fold, about 3-fold to about 25-fold, or about 4-fold to about 20-fold.

The immunogenic composition dose can be between 1 μg to 10 mg active component/kg body weight/time, and can be 20 μg to 10 mg component/kg body weight/time. The immunogenic composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of immunogenic composition doses for effective treatment can be 1, 2, 3, 4, 5, 6, 7, 8, 9, or 10.

The immunogenic composition can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration.

The immunogenic composition can be administered prophylactically or therapeutically. In prophylactic administration, the immunogenic compositions can be administered in an amount sufficient to induce an immune response. In therapeutic applications, the immunogenic compositions are administered to a subject in need thereof in an amount sufficient to elicit a therapeutic effect. An amount adequate to accomplish this is defined as "therapeutically effective dose." Amounts effective for this use will depend on, e.g., the particular composition of the immunogenic composition regimen administered, the manner of administration, the stage and severity of the disease, the general state of health of the subject, and the judgment of the prescribing physician.

The immunogenic composition can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the immunogenic composition can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The immunogenic composition can be delivered via a variety of routes. Typical delivery routes include parenteral administration, e.g., intradermal, intramuscular or subcutaneous delivery. Other routes include oral administration, intranasal, and intravaginal routes. For the DNA of the immunogenic composition in particular, the immunogenic composition can be delivered to the interstitial spaces of tissues of an individual (Felgner et al., U.S. Pat. Nos. 5,580,859 and 5,703,055, the contents of all of which are incorporated herein by reference in their entirety). The immunogenic composition can also be administered to muscle, or can be administered via intradermal or subcutaneous injections, or transdermally, such as by iontophoresis. Epidermal administration of the immunogenic composition can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The immunogenic composition can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the immunogenic composition.

The immunogenic composition can be a liquid preparation such as a suspension, syrup or elixir. The immunogenic composition can also be a preparation for parenteral, subcutaneous, intradermal, intramuscular or intravenous administration (e.g., injectable administration), such as a sterile suspension or emulsion.

The immunogenic composition can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The immunogenic composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The immunogenic composition may be administered by traditional syringes, needleless injection devices, "microprojectile bombardment gone guns", or other physical methods such as electroporation ("EP"), "hydrodynamic method", or ultrasound.

The plasmid of the immunogenic composition may be delivered to the mammal by several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The CCHFV antigen may be delivered via DNA injection and along with in vivo electroporation.

Electroporation

Administration of the immunogenic composition via electroporation may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the immunogenic compositions of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the immunogenic compositions include those provided in co-pending and co-owned U.S. patent application Ser. No. 11/874,072, filed Oct. 17, 2007, which claims the benefit under 35 USC 119 (e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

Method of Preparing the Vaccine

Provided herein are methods for preparing the DNA plasmids that comprise the vaccines discussed herein. The DNA plasmids, after the final subcloning step into the mammalian expression plasmid, can be used to inoculate a cell culture in a large-scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a US published application No. 20090004716, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

The present invention has multiple aspects, illustrated by the following non-limiting examples.

EXAMPLES

The present invention is further illustrated in the following Example. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: DNA Vaccine Targeting Crimean-Congo Hemorrhagic Fever Virus (CCHFV)

Figures 2A, 2B:
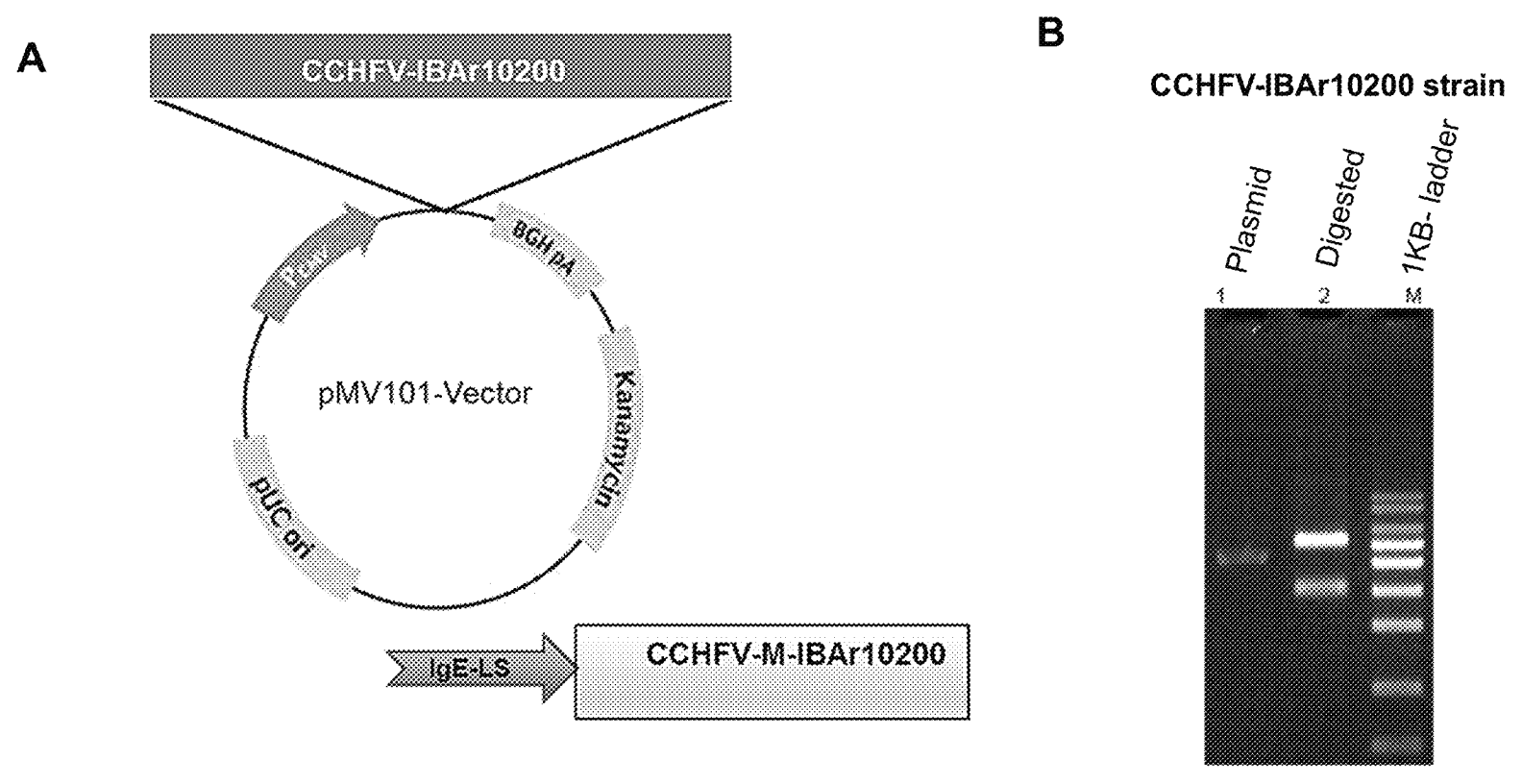
Figures 3A, 3B, 3C, 3D:
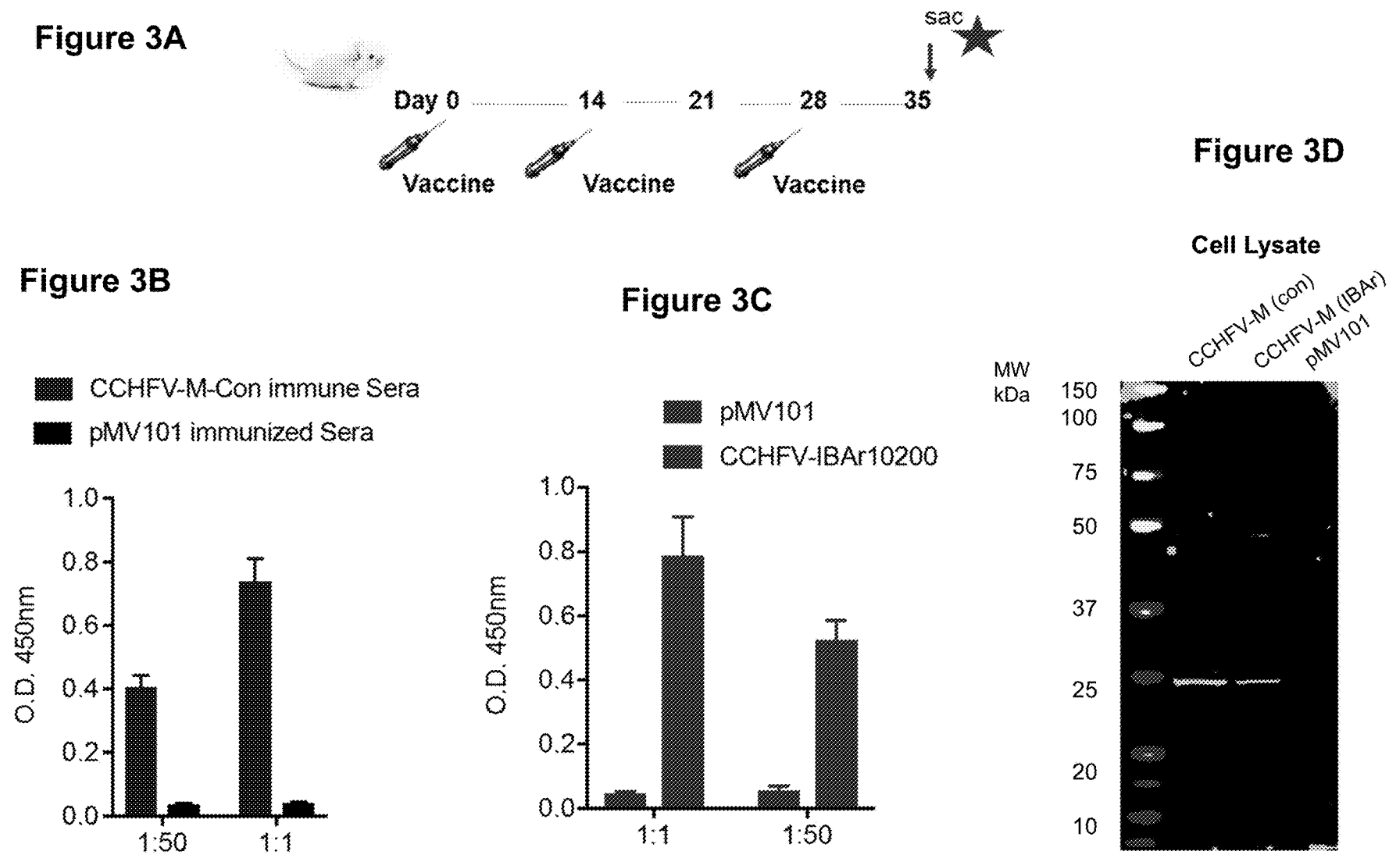
Figure 4:
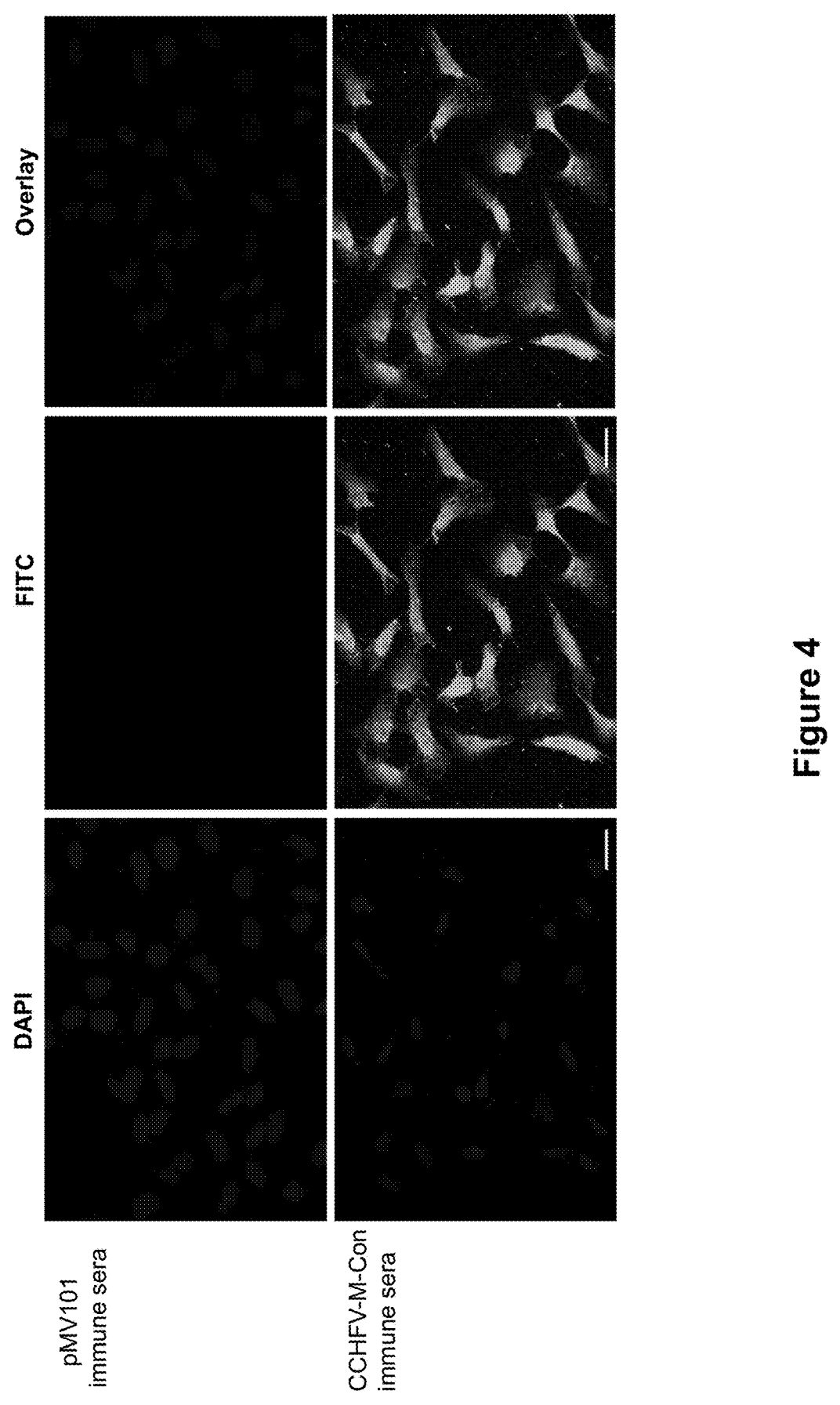
Figure 5B:
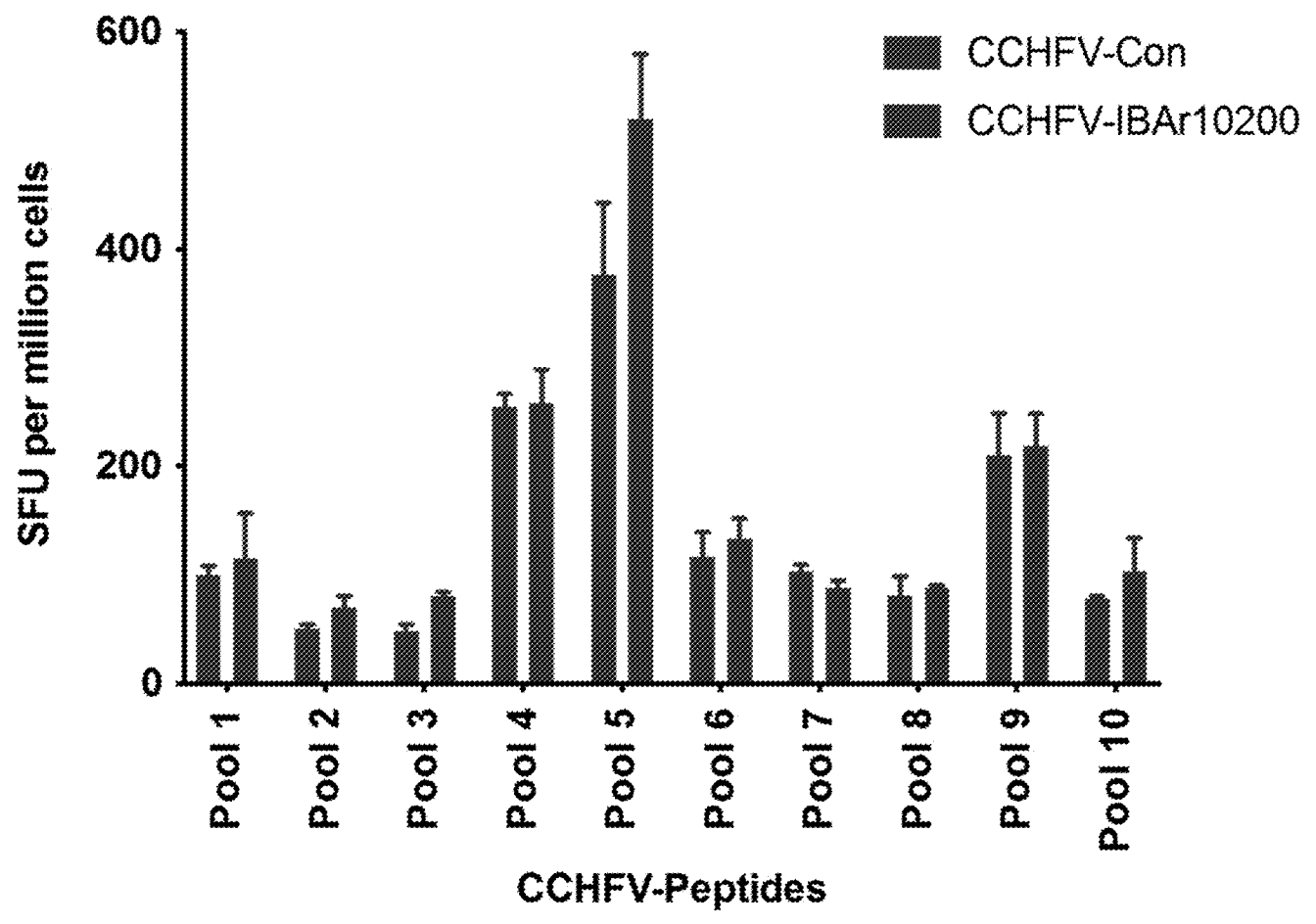

A DNA vaccine targeting Crimean-Congo hemorrhagic fever virus (CCHFV) virus has been developed. Optimized synthetic consensus CCHFV glycoprotein sequences were individually cloned into mammalian expression-plasmid DNA (FIG. 1 and FIG. 2) and delivered to mice via electroporation (FIG. 3). Following a single immunization, DNA vaccine constructs generated robust immune responses against CCHFV glycoprotein (FIG. 3 through FIG. 5). The vaccines are well expressed in vitro. Both CCHFV vaccines induce antibodies (FIG. 3).

In conclusion, this is the first construct of this kind and have shown that the CCHFV novel consensus DNA vaccine can be effectively delivered using in vivo EP, which results in the high levels of seroconversion (antibodies) in mice. The results demonstrate the virtual elimination for the need for using live-attenuated vaccines or viral chimeras or adeno-derived vectors. Further, synthetic enhanced CCHFV-DNA vaccine can be effectively delivered using in vivo electroporation, which results in the induction of immune responses including both cellular and humoral responses in the vaccinated mice.

Example 2: Consensus CCHFV Glycoprotein Sequences

Presented herein are the peptide sequences and the nucleic acid sequences for the peptides.

| SEQ ID NO: | Sequence type | Description |
|---|---|---|
| 1 | Nucleotide | CCHFV-Glycoprotein sequence |
| 2 | Amino acid | CCHFV-Glycoprotein sequence |
| 3 | Nucleotide | CCHFV-Glycoprotein operably linked to IgE leader sequence |
| 4 | Amino acid | CCHFV-Glycoprotein operably linked to IgE leader sequence |

What is claimed is:

1. A composition comprising: a nucleic acid molecule comprising a nucleotide sequence that encodes a consensus Crimean-Congo hemorrhagic fever virus (CCHFV) antigen wherein the antigen comprises the amino acid sequence selected from the group consisting of:
   a) SEQ ID NO:2, a fragment of SEQ ID NO:2 that comprises 600 or more consecutive amino acids; SEQ ID NO:2 linked to an IgE signal peptide, a fragment of SEQ ID NO:2 that comprises 600 or more consecutive amino acids linked to an IgE signal peptide; and
   b) SEQ ID NO:4, a fragment of SEQ ID NO:4 that comprises 600 or more consecutive amino acids, a fragment of SEQ ID NO:4 that comprises 600 or more consecutive amino acids linked to an IgE signal peptide.

2. The composition of claim 1 comprising a nucleotide sequence selected from the group consisting of:
   a) SEQ ID NO:1, a fragment of SEQ ID NO:1 that encodes 600 or more consecutive amino acids of SEQ ID NO:2, a nucleotide sequence that is at least 95% homologous to SEQ ID NO:1, a fragment of a nucleotide sequence that is at least 95% homologous to SEQ ID NO:1 that encodes 600 or more consecutive amino acids of SEQ ID NO:2; SEQ ID NO:1 operably linked to a nucleotide sequence that encodes an IgE signal peptide, a fragment of a nucleotide sequence that is at least 95% homologous to SEQ ID NO:1 that encodes 600 or more consecutive amino acids of SEQ ID NO:2 operably linked to a nucleotide sequence that encodes an IgE signal peptide, a nucleotide sequence that is at least 95% homologous to SEQ ID NO:1 that encodes an amino acid sequence that is at least 95% homologous to SEQ ID NO:2 operably linked to a nucleotide sequence that encodes an IgE signal peptide, and a fragment of a nucleotide sequence that is at least 95% homologous to SEQ ID NO:1 that encodes an amino acid sequence that is at least 95% homologous to SEQ ID NO:2 operably linked to a nucleotide sequence that encodes an IgE signal peptide; and
   b) SEQ ID NO:3, a fragment of SEQ ID NO:3 that encodes 600 or more consecutive amino acids of SEQ ID NO:4, a nucleotide sequence that is at least 95% homologous to SEQ ID NO:3, a fragment of a nucleotide sequence that is at least 95% homologous to SEQ ID NO:3 that encodes 600 or more consecutive amino acids of SEQ ID NO:4; SEQ ID NO:3 operably linked to a nucleotide sequence that encodes an IgE signal peptide, a fragment of a nucleotide sequence that is at least 95% homologous to SEQ ID NO:3 that encodes 600 or more consecutive amino acids of SEQ ID NO:4 operably linked to a nucleotide sequence that encodes an IgE signal peptide, a nucleotide sequence that is at least 95% homologous to SEQ ID NO:3 that encodes an amino acid sequence that is at least 95% homologous to SEQ ID NO:4 operably linked to a nucleotide sequence that encodes an IgE signal peptide, and a fragment of a nucleotide sequence that is at least 95% homologous to SEQ ID NO:3 that encodes an amino acid sequence that is at least 95% homologous to SEQ ID NO:4 operably linked to a nucleotide sequence that encodes an IgE signal peptide.

3. The composition of claim 1, wherein the nucleic acid molecule is an expression plasmid.

4. The composition of claim 1 formulated for delivery to an individual using electroporation.

5. The composition of claim 1 further comprising nucleic acid sequences that encode one or more proteins selected from the group consisting of: IL-12, IL-15 and IL-28.

6. A method of inducing an immune response against Crimean-Congo hemorrhagic fever virus (CCHFV) comprising administering the composition of claim 1 to an individual in an amount effective to induce an immune response in said individual.

7. A method of inducing an immune response in an individual who has been diagnosed with Crimean-Congo hemorrhagic fever virus (CCHFV) comprising administering a therapeutically effective amount of the composition of claim 1 to an individual in an amount effective to induce an immune response against CCHFV in the individual.

8. A method of inducing an immune response to Crimean-Congo hemorrhagic fever virus (CCHFV) infection in an individual comprising administering a prophylactically effective amount of the composition of claim 1 to an individual in an amount effective to induce an immune response against CCHFV in the individual.

9. The composition of claim 2, wherein the nucleic acid molecule is an expression plasmid.

10. The composition of claim 2 formulated for delivery to an individual using electroporation.

11. The composition of claim 2 further comprising nucleic acid sequences that encode one or more proteins selected from the group consisting of: IL-12, IL-15, and IL-28.

12. A method of inducing an immune response against Crimean-Congo hemorrhagic fever virus (CCHFV) comprising administering the composition of claim 2 to an individual in an amount effective to induce an immune response in said individual.

13. A method of inducing an immune response in an individual who has been diagnosed with Crimean-Congo hemorrhagic fever virus (CCHFV) comprising administering a therapeutically effective amount of the composition of claim 2 to an individual in an amount effective to induce an immune response against CCHFV in the individual.

14. A method of inducing an immune response to Crimean-Congo hemorrhagic fever virus (CCHFV) infection in an individual comprising administering a prophylactically effective amount of the composition of claim 2 to an individual in an amount effective to induce an immune response against CCHFV in the individual.

* * * * *

SEQUENCE LISTING

```
<160> NUMBER OF SEQ ID NOS: 14

<210> SEQ ID NO 1
<211> LENGTH: 5046
<212> TYPE: DNA
<213> ORGANISM: Artificial Sequence
<220> FEATURE:
<223> OTHER INFORMATION: Chemically Synthesized, CCHFV-Glycoprotein
      sequence

<400> SEQUENCE: 1
cacaccctgc tggtctgttt tattctgtat ctgcagctgt gcggcctggg cggcgcccac        60
ggaaacaata gcaacaccac agagcacaac accaatacca caaccctgg cagccagtcc       120 ccaagctcca agcctcccgt gagcacaacc ccctctatcc acaccctga gtctagcaca       180 aagccaacaa ccccaagcga gggcctggag ggctccggag aggtgtacac aaccccaccc       240
aacacaaccc agggcctgtc tcccagcgag acaaccccg agcctgccac aaccacaacc       300
acacagaacc caaccacagc cgatcccgac acatcctcta ccaattccac cacacaggat       360 accccacca cagtgacatc tcctagctcc tctccttcta caccaagcac ccctcaggga       420
caccaccctc cagtgcgctc cctgctgtct gtgagctccc caggaccaga cgagaagacc       480
acacctaccc caagcccgg cgagtctagc gagacacctt cctctcacag cgccagcagg       540
aggcctccca ccccacccac cacaacccag gtgagcaccg agaacaatag ccactccaca       600
ccaaggcagt ccgagagctc ccagccagcc acctctccag gcctgatgac aagcccagca       660
cagatcctga gcgcccttc cgccaccca atcgcaatcc aggataccca cccttcccca       720
acaaacaggt ctaagagaaa tctggagatg gagatcatcc tgacactgtc ccagggcctg       780
aagaagtact atggcaagat cctgaagctg ctgcacctga ccctggagga ggacacagag       840
ggcctgctgg agtggtgtaa gagaacctg ggctgagct gcgacgatga cttctttcag       900
aagcggatcg aggagttctt tatcaccggc gagggctact taatgaggt gctgcagttc       960
```

```
aagacactgt ctaccctgag ccctaccgag ccatctcacg caggcctgcc aacagcagag    1020 ccttcaaga gctattttgc caagggcttc ctgtccatcg attctggcta cttttccgcc     1080
aagtgttatc ccggcagatc tagctccggc ctgcagctga tcaacgtgac ccagcaccct    1140
gcaaggatcg cagagacacc aggacctaag acaacctccc tgaagaccat caactgcatc    1200
aatctgaggg ccagcgtgtt caaggagcac agagaggtgg agatcaatgt gctgctgcca    1260
cagatcgccg tgaacctgag caattgtcac gtggtcatca agtcccacgt gtgcgactac    1320
tctctggata ccgacggccc agtgagactg ccccacatca tccacgaggg caccttcatc    1380
cccggcacat ataagatcgt gatcgataag aagaacaagc tgaatgaccg tgtacactg     1440 gtgaccaact gcgtgatcaa gggaagggag gtgcgcaagg acagagcgt gctgcgccag     1500 tacaagaccg agatcaagat cggcaaggcc agcacaggct ccaggaagct gctgtccgag    1560
gagccaggcg atgactgtat ctctaggacc cagctgctga aacagagac agccgagatc     1620 cacgatgaca actacggcgg aacctggcgat aagatcacca tctgtaatgg cagcacaatc   1680
gtggaccagc gcctgggctc cgagctgggc tgctatacca tcaacagggt gaagtctttt    1740
aagctgtgcg agaatagcgc cacaggcaag acctgcgaga tcgactccac ccctgtgaag    1800
tgtcgccagg gcttctgcct gaagatcaca caggagggaa ggggacacgt gaagctgtct    1860
cgcggcagcg aggtggtgct ggatgcctgt gactctagct gcgaagtgat gatcccaaag    1920
ggcaccggcg atatcctggt ggactgcagc ggcggccagc agcacttcct gaaggataac    1980
ctgatcgacc tgggctgtcc caagatccct ctgctgggca gatggccat ctacatctgc     2040 agaatgagca atcaccctaa gacaaccatg gccttcctgt tttggttctc ctttggctac    2100
gtgatcacct gcatcttttg taaggccctg ttctatctgc tgatcatcat cggcacactg    2160
ggcaagcgga agaagcagta tcgcgagctg aagccccaga catgcaccat ctgtgagaca    2220
gcccctgtga acgccatcga tgccgagatg cacgacctga actgtagcta caatatctgc    2280
ccttattgtg ccagccggct gacctccgac ggcctggcaa ggcacgtgac acagtgccca    2340
aagaggaagg agaaggtgga ggagacagag ctgtacctga atctggagcg catcccctgg    2400
gtgcggagga agctgctgca ggtgtctgag agcaccggcg tggccctgaa gaggtcctct    2460
tggctgatcg tgctgctggt gctgctgaca gtgtccctgt ctcctgtgca gagcgcccca    2520
gtgggacacg gcaagacaat cgagacatat cagacacggg agggctttac ctccatctgt    2580
ctgttcatgc tgggcagcat cctgttcatc gtgtcctgcc tggtgaaggg cctggtggat    2640
agcgtgtcca actcttttctt tccaggcctg tccgtgtgca agacatgttc catcggctct    2700
atcaatggct ttgagatcga gtctcacaag tgctactgta gcctgttctg ctgtccctat    2760
tgccggcact gttctgccga ccgcgagatc caccagctgc acctgtctat ctgcaagaag    2820
aggaagaccg gcagcaacgt gatgctggcc gtgtgcaagc ggatgtgctt tagggcaaca    2880
gaggccagct ccaacagggc cctgctgatc agatccatca tcaatacaac cttcgtgatc    2940
tgtatcctga ccctggccat ctgcgtggtg agcacatccg ccgtggagat ggagaatctg    3000
ccagccggca cctgggagag agaggaggat ctgacaaaact tttgtcacca ggagtgccag    3060
gtgacagaga cagagtgcct gtgcccatac gaggccctgg tgctgaggaa gcctctgttc    3120
ctggacagca tcgtgaaggg catgaagaac ctgctgaatt ctaccagcct ggagacatcc    3180
ctgtctatcg aggccccatg gggcgccatc aacgtgcagt ccacctttaa gcccaccgtg    3240
tctacagcca atatcgccct gagctggtct agcgtggagc acagaggcaa caagatcctg    3300
```

```
gtgaccggcc ggagcgagtc catcatgaag ctggaggaga gaacaggcgt gtcctgggat    3360
ctgggcgtgg aggacgcctc tgagagcaag ctgctgaccg tgtctatcat ggacctgtct    3420
cagatgtaca gccccgtgtt cgagtatctg agcggcgata caggtggga ggagtggcca    3480 aaggcaacat gtaccggcga ctgcccagag cggtgcggat gtacctcctc tacatgtctg    3540
cacaaggagt ggcctcacag caggaactgg agatgtaatc aacctggtg ctggggcgtg    3600 ggaaccggat gcacatgctg tggcgtggat gtgaaggacc tgtttacaga tcacatgttc    3660
gtgaagtgga aggtggagta catcaagacc gaggccatcg tgtgcgtgga gctgacatcc    3720
caggagagac agtgctctct gatcgaggca ggaacccggt tcaatctggg accagtgaca    3780
atcaccctgt ccgagcccag aaacatccag cagaagctgc tccagagat catcacactg    3840 caccctaaga tcgaggaggg cttctttgac ctgatgcacg tgcagaaggt gctgtccgcc    3900
tctaccgtgt gcaagctgca gagctgcaca cacggcatcc caggcgatct gcaggtgtat    3960
cacatcggca acctgctgaa gggcgaccgg gtgaatggcc acctgatcca aagatcgag    4020 cctcactta ataccagctg gatgtcctgg gatggctgtg atctggacta ctattgcaac    4080
atgggcgact ggccatcttg tacatacacc ggcgtgaccc agcacaatca cgccgccttc    4140
gtgaacctgc tgaatatcga cagattat acaaagacct ccactttca cagcaagcgc    4200 gtgaccgccc acggcgatac acctcagctg gacctgaagg ccaggccaac ctacggagca    4260
ggcgagatca cagtgctggt ggaggtggcc gacatgagc tgcacaccaa gaaggtggag    4320
atcagcggcc tgaagttcgc ctccctgaca tgcaccggct gttatgcctg cagctccggc    4380
atctcctgca aggtgagaat ccacgtggat gagcctgacg agctgaccgt gcacgtgaag    4440
tctagcgatc cagacgtggt ggcagcctcc tctctgatgg cacgcaagct ggagtttggc    4500
accgattcta cattcaaggc ctttagcgcc atgcccaaga cctccctgtg cttctacatc    4560
gtggagaggg agtattgtaa gagctgctcc gaggaggata cccagaagtg cgtggacaca    4620
aagctggagc agcctcagag catcctgatc gagcacaagg gcaccatcat cggcaagcag    4680
aacgacacat gtaccgccaa ggcctcctgc tggctggagt ctgtgaagag cttctttac    4740 ggcctgaaga acatgctggg cagcgtgttc ggcaacgtgt tcatcggcat cctgctgttt    4800 ctggcccct tcgtgctgct gatcctgttc tttatgtttg gctggaagat cctgttctgc    4860
tttaagtgct gtaggagaac caggggcctg ttcaagtaca gacacctgaa ggatgacgag    4920
gagacaggct atcggcgcat catcgagcgc ctgaacaata agaagggcaa gaacaggctg    4980
ctggacggag agcggctggc tgatagaaaa atcgcagaac tgtttagcac aaagactcac    5040
atcgga                                                                5046
```

`<210>` SEQ ID NO 2
`<211>` LENGTH: 1682
`<212>` TYPE: PRT
`<213>` ORGANISM: Artificial Sequence
`<220>` FEATURE:
`<223>` OTHER INFORMATION: Chemically Synthesized, CCHFV-Glycoprotein
        sequence

`<400>` SEQUENCE: 2

His Thr Leu Leu Val Cys Phe Ile Leu Tyr Leu Gln Leu Cys Gly Leu
1               5                   10                  15

Gly Gly Ala His Gly Asn Asn Ser Asn Thr Thr Glu His Asn Thr Asn
            20                  25                  30

Thr Thr Thr Pro Gly Ser Gln Ser Pro Ser Ser Lys Pro Pro Val Ser
        35                  40                  45

```
Thr Thr Pro Ser Ile His Thr Pro Glu Ser Ser Thr Lys Pro Thr Thr
 50                  55                  60
Pro Ser Glu Gly Leu Glu Gly Ser Gly Glu Val Tyr Thr Thr Pro Pro
 65                  70                  75                  80
Asn Thr Thr Gln Gly Leu Ser Pro Ser Glu Thr Thr Pro Glu Pro Ala
                 85                  90                  95
Thr Thr Thr Thr Thr Gln Asn Pro Thr Thr Ala Asp Pro Asp Thr Ser
                100                 105                 110
Ser Thr Asn Ser Thr Thr Gln Asp Thr Pro Thr Thr Val Thr Ser Pro
             115                 120                 125
Ser Ser Ser Pro Ser Thr Pro Ser Thr Pro Gln Gly His His Pro Pro
             130                 135                 140
Val Arg Ser Leu Leu Ser Val Ser Ser Pro Gly Pro Asp Glu Lys Thr
145                 150                 155                 160
Thr Pro Thr Pro Ser Pro Gly Glu Ser Ser Glu Thr Pro Ser Ser His
                165                 170                 175
Ser Ala Ser Arg Arg Pro Pro Thr Pro Pro Thr Thr Thr Gln Val Ser
             180                 185                 190
Thr Glu Asn Asn Ser His Ser Thr Pro Arg Gln Ser Glu Ser Ser Gln
             195                 200                 205
Pro Ala Thr Ser Pro Gly Leu Met Thr Ser Pro Ala Gln Ile Leu Ser
             210                 215                 220
Ala Pro Ser Ala Thr Pro Ile Ala Ile Gln Asp Thr His Pro Ser Pro
225                 230                 235                 240
Thr Asn Arg Ser Lys Arg Asn Leu Glu Met Glu Ile Ile Leu Thr Leu
                245                 250                 255
Ser Gln Gly Leu Lys Lys Tyr Tyr Gly Lys Ile Leu Lys Leu Leu His
             260                 265                 270
Leu Thr Leu Glu Glu Asp Thr Glu Gly Leu Leu Glu Trp Cys Lys Arg
             275                 280                 285
Asn Leu Gly Leu Ser Cys Asp Asp Phe Phe Gln Lys Arg Ile Glu
             290                 295                 300
Glu Phe Phe Ile Thr Gly Glu Gly Tyr Phe Asn Glu Val Leu Gln Phe
305                 310                 315                 320
Lys Thr Leu Ser Thr Leu Ser Pro Thr Glu Pro Ser His Ala Gly Leu
                325                 330                 335
Pro Thr Ala Glu Pro Phe Lys Ser Tyr Phe Ala Lys Gly Phe Leu Ser
             340                 345                 350
Ile Asp Ser Gly Tyr Phe Ser Ala Lys Cys Tyr Pro Gly Arg Ser Ser
             355                 360                 365
Ser Gly Leu Gln Leu Ile Asn Val Thr Gln His Pro Ala Arg Ile Ala
             370                 375                 380
Glu Thr Pro Gly Pro Lys Thr Thr Ser Leu Lys Thr Ile Asn Cys Ile
385                 390                 395                 400
Asn Leu Arg Ala Ser Val Phe Lys Glu His Arg Glu Val Glu Ile Asn
                405                 410                 415
Val Leu Leu Pro Gln Ile Ala Val Asn Leu Ser Asn Cys His Val Val
             420                 425                 430
Ile Lys Ser His Val Cys Asp Tyr Ser Leu Asp Thr Asp Gly Pro Val
             435                 440                 445
Arg Leu Pro His Ile Ile His Glu Gly Thr Phe Ile Pro Gly Thr Tyr
             450                 455                 460
```

```
Lys Ile Val Ile Asp Lys Lys Asn Lys Leu Asn Asp Arg Cys Thr Leu
465                 470                 475                 480

Val Thr Asn Cys Val Ile Lys Gly Arg Glu Val Arg Lys Gly Gln Ser
            485                 490                 495

Val Leu Arg Gln Tyr Lys Thr Glu Ile Lys Ile Gly Lys Ala Ser Thr
        500                 505                 510

Gly Ser Arg Lys Leu Leu Ser Glu Glu Pro Gly Asp Cys Ile Ser
    515                 520                 525

Arg Thr Gln Leu Leu Arg Thr Glu Ala Glu Ile His Asp Asp Asn
530                 535                 540

Tyr Gly Gly Pro Gly Asp Lys Ile Thr Ile Cys Asn Gly Ser Thr Ile
545                 550                 555                 560

Val Asp Gln Arg Leu Gly Ser Glu Leu Gly Cys Tyr Thr Ile Asn Arg
            565                 570                 575

Val Lys Ser Phe Lys Leu Cys Glu Asn Ser Ala Thr Gly Lys Thr Cys
        580                 585                 590

Glu Ile Asp Ser Thr Pro Val Lys Cys Arg Gln Gly Phe Cys Leu Lys
    595                 600                 605

Ile Thr Gln Glu Gly Arg Gly His Val Lys Leu Ser Arg Gly Ser Glu
610                 615                 620

Val Val Leu Asp Ala Cys Asp Ser Ser Cys Glu Val Met Ile Pro Lys
625                 630                 635                 640

Gly Thr Gly Asp Ile Leu Val Asp Cys Ser Gly Gly Gln Gln His Phe
            645                 650                 655

Leu Lys Asp Asn Leu Ile Asp Leu Gly Cys Pro Lys Ile Pro Leu Leu
        660                 665                 670

Gly Lys Met Ala Ile Tyr Ile Cys Arg Met Ser Asn His Pro Lys Thr
    675                 680                 685

Thr Met Ala Phe Leu Phe Trp Phe Ser Phe Gly Tyr Val Ile Thr Cys
690                 695                 700

Ile Phe Cys Lys Ala Leu Phe Tyr Leu Ile Ile Ile Gly Thr Leu
705                 710                 715                 720

Gly Lys Arg Lys Lys Gln Tyr Arg Glu Leu Lys Pro Gln Thr Cys Thr
            725                 730                 735

Ile Cys Glu Thr Ala Pro Val Asn Ala Ile Asp Ala Glu Met His Asp
        740                 745                 750

Leu Asn Cys Ser Tyr Asn Ile Cys Pro Tyr Cys Ala Ser Arg Leu Thr
    755                 760                 765

Ser Asp Gly Leu Ala Arg His Val Thr Gln Cys Pro Lys Arg Lys Glu
770                 775                 780

Lys Val Glu Glu Thr Glu Leu Tyr Leu Asn Leu Glu Arg Ile Pro Trp
785                 790                 795                 800

Val Arg Arg Lys Leu Leu Gln Val Ser Glu Ser Thr Gly Val Ala Leu
            805                 810                 815

Lys Arg Ser Ser Trp Leu Ile Val Leu Leu Val Leu Thr Val Ser
        820                 825                 830

Leu Ser Pro Val Gln Ser Ala Pro Val Gly His Gly Lys Thr Ile Glu
    835                 840                 845

Thr Tyr Gln Thr Arg Glu Gly Phe Thr Ser Ile Cys Leu Phe Met Leu
850                 855                 860

Gly Ser Ile Leu Phe Ile Val Ser Cys Leu Val Lys Gly Leu Val Asp
865                 870                 875                 880

Ser Val Ser Asn Ser Phe Phe Pro Gly Leu Ser Val Cys Lys Thr Cys
```

```
                      885                 890                 895
        Ser Ile Gly Ser Ile Asn Gly Phe Glu Ile Glu Ser His Lys Cys Tyr
                          900                 905                 910

Cys Ser Leu Phe Cys Cys Pro Tyr Cys Arg His Cys Ser Ala Asp Arg
                          915                 920                 925

Glu Ile His Gln Leu His Leu Ser Ile Cys Lys Lys Arg Lys Thr Gly
                          930                 935                 940

Ser Asn Val Met Leu Ala Val Cys Lys Arg Met Cys Phe Arg Ala Thr
        945                 950                 955                 960

Glu Ala Ser Ser Asn Arg Ala Leu Leu Ile Arg Ser Ile Ile Asn Thr
                          965                 970                 975

Thr Phe Val Ile Cys Ile Leu Thr Leu Ala Ile Cys Val Val Ser Thr
                          980                 985                 990

Ser Ala Val Glu Met Glu Asn Leu Pro Ala Gly Thr Trp Glu Arg Glu
                          995                1000                1005

Glu Asp Leu Thr Asn Phe Cys His Gln Glu Cys Gln Val Thr Glu
            1010                1015                1020

Thr Glu Cys Leu Cys Pro Tyr Glu Ala Leu Val Leu Arg Lys Pro
            1025                1030                1035

Leu Phe Leu Asp Ser Ile Val Lys Gly Met Lys Asn Leu Leu Asn
            1040                1045                1050

Ser Thr Ser Leu Glu Thr Ser Leu Ser Ile Glu Ala Pro Trp Gly
            1055                1060                1065

Ala Ile Asn Val Gln Ser Thr Phe Lys Pro Thr Val Ser Thr Ala
            1070                1075                1080

Asn Ile Ala Leu Ser Trp Ser Ser Val Glu His Arg Gly Asn Lys
            1085                1090                1095

Ile Leu Val Thr Gly Arg Ser Glu Ser Ile Met Lys Leu Glu Glu
            1100                1105                1110

Arg Thr Gly Val Ser Trp Asp Leu Gly Val Glu Asp Ala Ser Glu
            1115                1120                1125

Ser Lys Leu Leu Thr Val Ser Ile Met Asp Leu Ser Gln Met Tyr
            1130                1135                1140

Ser Pro Val Phe Glu Tyr Leu Ser Gly Asp Arg Gln Val Glu Glu
            1145                1150                1155

Trp Pro Lys Ala Thr Cys Thr Gly Asp Cys Pro Glu Arg Cys Gly
            1160                1165                1170

Cys Thr Ser Ser Thr Cys Leu His Lys Glu Trp Pro His Ser Arg
            1175                1180                1185

Asn Trp Arg Cys Asn Pro Thr Trp Cys Trp Gly Val Gly Thr Gly
            1190                1195                1200

Cys Thr Cys Cys Gly Val Asp Val Lys Asp Leu Phe Thr Asp His
            1205                1210                1215

Met Phe Val Lys Trp Lys Val Glu Tyr Ile Lys Thr Glu Ala Ile
            1220                1225                1230

Val Cys Val Glu Leu Thr Ser Gln Glu Arg Gln Cys Ser Leu Ile
            1235                1240                1245

Glu Ala Gly Thr Arg Phe Asn Leu Gly Pro Val Thr Ile Thr Leu
            1250                1255                1260

Ser Glu Pro Arg Asn Ile Gln Gln Lys Leu Pro Pro Glu Ile Ile
            1265                1270                1275

Thr Leu His Pro Lys Ile Glu Glu Gly Phe Phe Asp Leu Met His
            1280                1285                1290
```

```
Val Gln Lys Val Leu Ser Ala Ser Thr Val Cys Lys Leu Gln Ser
    1295            1300                1305

Cys Thr His Gly Ile Pro Gly Asp Leu Gln Val Tyr His Ile Gly
    1310            1315                1320

Asn Leu Leu Lys Gly Asp Arg Val Asn Gly His Leu Ile His Lys
    1325            1330                1335

Ile Glu Pro His Phe Asn Thr Ser Trp Met Ser Trp Asp Gly Cys
    1340            1345                1350

Asp Leu Asp Tyr Tyr Cys Asn Met Gly Asp Trp Pro Ser Cys Thr
    1355            1360                1365

Tyr Thr Gly Val Thr Gln His Asn His Ala Ala Phe Val Asn Leu
    1370            1375                1380

Leu Asn Ile Glu Thr Asp Tyr Thr Lys Thr Phe His Phe His Ser
    1385            1390                1395

Lys Arg Val Thr Ala His Gly Asp Thr Pro Gln Leu Asp Leu Lys
    1400            1405                1410

Ala Arg Pro Thr Tyr Gly Ala Gly Glu Ile Thr Val Leu Val Glu
    1415            1420                1425

Val Ala Asp Met Glu Leu His Thr Lys Lys Val Glu Ile Ser Gly
    1430            1435                1440

Leu Lys Phe Ala Ser Leu Thr Cys Thr Gly Cys Tyr Ala Cys Ser
    1445            1450                1455

Ser Gly Ile Ser Cys Lys Val Arg Ile His Val Asp Glu Pro Asp
    1460            1465                1470

Glu Leu Thr Val His Val Lys Ser Ser Asp Pro Asp Val Val Ala
    1475            1480                1485

Ala Ser Ser Leu Met Ala Arg Lys Leu Glu Phe Gly Thr Asp Ser
    1490            1495                1500

Thr Phe Lys Ala Phe Ser Ala Met Pro Lys Thr Ser Leu Cys Phe
    1505            1510                1515

Tyr Ile Val Glu Arg Glu Tyr Cys Lys Ser Cys Ser Glu Glu Asp
    1520            1525                1530

Thr Gln Lys Cys Val Asp Thr Lys Leu Glu Gln Pro Gln Ser Ile
    1535            1540                1545

Leu Ile Glu His Lys Gly Thr Ile Ile Gly Lys Gln Asn Asp Thr
    1550            1555                1560

Cys Thr Ala Lys Ala Ser Cys Trp Leu Glu Ser Val Lys Ser Phe
    1565            1570                1575

Phe Tyr Gly Leu Lys Asn Met Leu Gly Ser Val Phe Gly Asn Val
    1580            1585                1590

Phe Ile Gly Ile Leu Leu Phe Leu Ala Pro Phe Val Leu Leu Ile
    1595            1600                1605

Leu Phe Phe Met Phe Gly Trp Lys Ile Leu Phe Cys Phe Lys Cys
    1610            1615                1620

Cys Arg Arg Thr Arg Gly Leu Phe Lys Tyr Arg His Leu Lys Asp
    1625            1630                1635

Asp Glu Glu Thr Gly Tyr Arg Arg Ile Ile Glu Arg Leu Asn Asn
    1640            1645                1650

Lys Lys Gly Lys Asn Arg Leu Leu Asp Gly Glu Arg Leu Ala Asp
    1655            1660                1665

Arg Lys Ile Ala Glu Leu Phe Ser Thr Lys Thr His Ile Gly
    1670            1675                1680
```

<210> SEQ ID NO 3
<211> LENGTH: 5106
<212> TYPE: DNA
<213> ORGANISM: Artificial Sequence
<220> FEATURE:
<223> OTHER INFORMATION: Chemically Synthesized, CCHFV-Glycoprotein
      operably linked to IgE leader sequence and two stop codons

<400> SEQUENCE: 3

| | | | | | |
|---|---|---|---|---|---|
| atggactgga | cttggattct | gtttctggtc | gccgccgcta | cccgagtgca | ttctcacacc     60 |
| ctgctggtct | gttttattct | gtatctgcag | ctgtgcggcc | tgggcggcgc | ccacggaaac    120 |
| aatagcaaca | ccacagagca | aacaccaat | accacaaccc | ctggcagcca | gtccccaagc    180 |
| tccaagcctc | ccgtgagcac | aaccccctct | atccacaccc | ctgagtctag | cacaaagcca    240 |
| acaaccccaa | gcgagggcct | ggagggctcc | ggagaggtgt | acacaacccc | acccaacaca    300 |
| acccagggcc | tgtctcccag | cgagacaacc | cccgagcctg | ccacaaccac | aaccacacag    360 |
| aacccaacca | cagccgatcc | cgacacatcc | tctaccaatt | ccaccacaca | ggatacccc     420 |
| accacagtga | catctcctag | ctcctctcct | tctacaccaa | gcacccctca | gggacaccac    480 |
| cctccagtgc | gctcccctgct | gtctgtgagc | tccccaggac | cagacgagaa | gaccacacct    540 |
| accccaagcc | ccggcgagtc | tagcgagaca | ccttcctctc | acagcgccag | caggaggcct    600 |
| cccaccccac | ccaccacaac | ccaggtgagc | accgagaaca | tagccactc | cacaccaagg     660 |
| cagtccgaga | gctcccagcc | agccacctct | ccaggcctga | tgacaagccc | agcacagatc    720 |
| ctgagcgccc | cttccgccac | cccaatcgca | atccaggata | cccacccttc | ccaacaaac     780 |
| aggtctaaga | gaaatctgga | gatggagatc | atcctgacac | tgtcccaggg | cctgaagaag    840 |
| tactatggca | agatcctgaa | gctgctgcac | ctgacccctgg | aggaggacac | agagggcctg    900 |
| ctggagtggt | gtaagagaaa | acctgggcctg | agctgcgacg | atgacttctt | tcagaagcgg    960 |
| atcgaggagt | tctttatcac | cggcgagggc | tactttaatg | aggtgctgca | gttcaagaca   1020 |
| ctgtctaccc | tgagccctac | cgagccatct | cacgcaggcc | tgccaacagc | agagcctttc   1080 |
| aagagctatt | ttgccaaggg | cttcctgtcc | atcgattctg | ctactttcc | cgccaagtgt   1140 |
| tatcccggca | gatctagctc | cggcctgcag | ctgatcaacg | tgacccagca | ccctgcaagg   1200 |
| atcgcagaga | caccaggacc | taagacaaac | tccctgaaga | ccatcaactg | catcaatctg   1260 |
| agggccagcg | tgttcaagga | gcacagagag | gtggagatca | tgtgctgct | ccacagatc   1320 |
| gccgtgaacc | tgagcaattg | tcacgtggtc | atcaagtccc | acgtgtgcga | ctactctctg   1380 |
| gataccgacg | gccagtgag | actgccccac | atcatccacg | agggcacctt | catcccggc   1440 |
| acatataaga | tcgtgatcga | taagaagaac | aagctgaatg | accggtgtac | actggtgacc   1500 |
| aactgcgtga | tcaagggaag | ggaggtgcgc | aagggcagag | cgtgctgcg | ccagtacaag   1560 |
| accgagatca | agatcggcaa | ggccagcaca | ggctccagga | agctgctgtc | cgaggagcca   1620 |
| ggcgatgact | gtatctctag | gacccagctg | ctgagaacag | agacagccga | gatccacgat   1680 |
| gacaactacg | gcggacctgg | cgataagatc | accatctgta | atggcagcac | aatcgtggac   1740 |
| cagcgcctgg | gctccgagct | gggctgctat | accatcaaca | gggtgaagtc | ttttaagctg   1800 |
| tgcgagaata | gcgccacagg | caagacctgc | gagatcgact | ccacccctgt | gaagtgtcgc   1860 |
| cagggcttct | gcctgaagat | cacacaggag | ggaagggac | acgtgaagct | gtctcgcggc   1920 |
| agcgaggtgg | tgctggatgc | ctgtgactct | agctgcgaag | tgatgatccc | aaagggcacc   1980 |
| ggcgatatcc | tggtggactg | cagcggcggc | cagcagcact | cctgaaggaa | taacctgatc   2040 |

-continued

```
gacctgggct gtcccaagat ccctctgctg ggcaagatgg ccatctacat ctgcagaatg   2100
agcaatcacc ctaagacaac catggccttc ctgttttggt tctcctttgg ctacgtgatc   2160
acctgcatct tttgtaaggc cctgttctat ctgctgatca tcatcggcac actgggcaag   2220
cggaagaagc agtatcgcga gctgaagccc cagacatgca ccatctgtga cagcccct     2280 gtgaacgcca tcgatgccga gatgcacgac ctgaactgta gctacaatat ctgcccttat   2340
tgtgccagcc ggctgacctc cgacggcctg caaggcacg tgacacagtg cccaaagagg    2400
aaggagaagg tggaggagac agagctgtac ctgaatctgg agcgcatccc ctgggtgcgg   2460
aggaagctgc tgcaggtgtc tgagagcacc ggcgtggccc tgaagaggtc ctcttggctg   2520
atcgtgctgc tggtgctgct gacagtgtcc ctgtctcctg tgcagagcgc cccagtggga   2580
cacggcaaga caatcgagac atatcagaca cgggagggct ttacctccat ctgtctgttc   2640
atgctgggca gcatcctgtt catcgtgtcc tgcctggtga agggcctggt ggatagcgtg   2700
tccaactctt tctttccagg cctgtccgtg tgcaagacat gttccatcgg ctctatcaat   2760
ggctttgaga tcgagtctca caagtgctac tgtagcctgt tctgctgtcc ctattgccgg   2820
cactgttctg ccgaccgcga gatccaccag ctgcacctgt ctatctgcaa gaagaggaag   2880
accggcagca acgtgatgct ggccgtgtgc aagcggatgt gctttagggc aacagaggcc   2940
agctccaaca gggccctgct gatcagatcc atcatcaata caaccttcgt gatctgtatc   3000
ctgaccctgg ccatctgcgt ggtgagcaca tccgccgtgg agatggagaa tctgccagcc   3060
ggcacctggg agagagagga ggatctgaca aacttttgtc accaggagtg ccaggtgaca   3120
gagacagagt gcctgtgccc atacgaggcc ctggtgctga ggaagcctct gttcctggac   3180
agcatcgtga agggcatgaa gaacctgctg aattctacca gcctggagac atccctgtct   3240
atcgaggccc catggggcgc catcaacgtg cagtccacct ttaagcccac cgtgtctaca   3300
gccaatatcg ccctgagctg gtctagcgtg gagcacagag caacaagat cctggtgacc    3360 ggccggagcg agtccatcat gaagctggag gagagaacag gcgtgtcctg ggatctgggc   3420
gtggaggacg cctctgagag caagctgctg accgtgtcta tcatggacct gtctcagatg   3480
tacagccccg tgttcgagta tctgagcggg atagacagg tggaggagtg gccaaaggca    3540
acatgtaccg gcgactgccc agagcggtgc ggatgtacct cctctacatg tctgcacaag   3600
gagtggcctc acagcaggaa ctggagatgt aatccaacct ggtgctgggg cgtgggaacc   3660
ggatgcacat gctgtggcgt ggatgtgaag gacctgttta cagatcacat gttcgtgaag   3720
tggaaggtgg agtacatcaa gaccgaggcc atcgtgtgcg tggagctgac atcccaggag   3780
agacagtgct ctctgatcga ggcaggaacc cggttcaatc tgggaccagt gacaatcacc   3840
ctgtccgagc ccagaaacat ccagcagaag ctgcctccag agatcatcac actgcaccct   3900
aagatcgagg agggcttctt tgacctgatg cacgtgcaga aggtgctgtc cgcctctacc   3960
gtgtgcaagc tgcagagctg cacacacggc atcccaggcg atctgcaggt gtatcacatc   4020
ggcaacctgc tgaagggcga ccgggtgaat ggccacctga tccacaagat cgagcctcac   4080
tttaatacca gctggatgtc ctgggatggc tgtgatctgg actactattg caacatgggc   4140
gactggccat cttgtacata caccggcgtg acccagcaca atcacgccgc cttcgtgaac   4200
ctgctgaata tcgagacaga ttatacaaag accttccact tcacagcaa gcgcgtgacc    4260 gcccacggcg atacacctca gctggacctg aaggccaggc caacctacgg agcaggcgag   4320
atcacagtgc tggtggaggt ggccgacatg gagctgcaca ccaagaaggt ggagatcagc   4380
ggcctgaagt tcgcctccct gacatgcacc ggctgttatg cctgcagctc cggcatctcc   4440
```

```
tgcaaggtga gaatccacgt ggatgagcct gacgagctga ccgtgcacgt gaagtctagc    4500
gatccagacg tggtggcagc ctcctctctg atggcacgca agctggagtt tggcaccgat    4560
tctacattca aggcctttag cgccatgccc aagacctccc tgtgcttcta catcgtggag    4620
agggagtatt gtaagagctg ctccgaggag gatacccaga agtgcgtgga cacaaagctg    4680
gagcagcctc agagcatcct gatcgagcac aagggcacca tcatcggcaa gcagaacgac    4740
acatgtaccg ccaaggcctc ctgctggctg gagtctgtga agagcttctt ttacggcctg    4800
aagaacatgc tgggcagcgt gttcggcaac gtgttcatcg gcatcctgct gtttctggcc    4860
cccttcgtgc tgctgatcct gttctttatg tttggctgga agatcctgtt ctgctttaag    4920
tgctgtagga gaaccagggg cctgttcaag tacagacacc tgaaggatga cgaggagaca    4980
ggctatcggc gcatcatcga gcgcctgaac aataagaagg gcaagaacag gctgctggac    5040
ggagagcggc tggctgatag aaaaatcgca gaactgttta gcacaaagac tcacatcgga    5100
taatga                                                               5106
```

<210> SEQ ID NO 4
<211> LENGTH: 1700
<212> TYPE: PRT
<213> ORGANISM: Artificial Sequence
<220> FEATURE:
<223> OTHER INFORMATION: Chemically Synthesized, CCHFV-Glycoprotein
      operably linked to IgE leader sequence and two stop codons

<400> SEQUENCE: 4

```
Met Asp Trp Thr Trp Ile Leu Phe Leu Val Ala Ala Thr Arg Val
1               5                   10                  15

His Ser His Thr Leu Leu Val Cys Phe Ile Leu Tyr Leu Gln Leu Cys
                20                  25                  30

Gly Leu Gly Gly Ala His Gly Asn Asn Ser Asn Thr Thr Glu His Asn
            35                  40                  45

Thr Asn Thr Thr Thr Pro Gly Ser Gln Ser Pro Ser Lys Pro
50                  55                  60

Val Ser Thr Thr Pro Ser Ile His Thr Pro Glu Ser Ser Thr Lys Pro
65                  70                  75                  80

Thr Thr Pro Ser Glu Gly Leu Glu Gly Ser Gly Glu Val Tyr Thr Thr
                85                  90                  95

Pro Pro Asn Thr Thr Gln Gly Leu Ser Pro Ser Glu Thr Thr Pro Glu
                100                 105                 110

Pro Ala Thr Thr Thr Thr Gln Asn Pro Thr Ala Asp Pro Asp
            115                 120                 125

Thr Ser Ser Thr Asn Ser Thr Thr Gln Asp Thr Pro Thr Thr Val Thr
                130                 135                 140

Ser Pro Ser Ser Ser Pro Ser Thr Pro Ser Thr Pro Gln Gly His His
145                 150                 155                 160

Pro Pro Val Arg Ser Leu Leu Ser Val Ser Ser Pro Gly Pro Asp Glu
                165                 170                 175

Lys Thr Thr Pro Thr Pro Ser Pro Gly Glu Ser Ser Glu Thr Pro Ser
                180                 185                 190

Ser His Ser Ala Ser Arg Arg Pro Pro Thr Pro Thr Thr Thr Gln
                195                 200                 205

Val Ser Thr Glu Asn Asn Ser His Ser Thr Pro Arg Gln Ser Glu Ser
            210                 215                 220

Ser Gln Pro Ala Thr Ser Pro Gly Leu Met Thr Ser Pro Ala Gln Ile
```

```
             225                 230                 235                 240
Leu Ser Ala Pro Ser Ala Thr Pro Ile Ala Ile Gln Asp Thr His Pro
                 245                 250                 255

Ser Pro Thr Asn Arg Ser Lys Arg Asn Leu Glu Met Glu Ile Ile Leu
                 260                 265                 270

Thr Leu Ser Gln Gly Leu Lys Lys Tyr Tyr Gly Lys Ile Leu Lys Leu
                 275                 280                 285

Leu His Leu Thr Leu Glu Glu Asp Thr Glu Gly Leu Leu Glu Trp Cys
             290                 295                 300

Lys Arg Asn Leu Gly Leu Ser Cys Asp Asp Phe Phe Gln Lys Arg
305                 310                 315                 320

Ile Glu Glu Phe Phe Ile Thr Gly Glu Gly Tyr Phe Asn Glu Val Leu
                 325                 330                 335

Gln Phe Lys Thr Leu Ser Thr Leu Ser Pro Thr Glu Pro Ser His Ala
                 340                 345                 350

Gly Leu Pro Thr Ala Glu Pro Phe Lys Ser Tyr Phe Ala Lys Gly Phe
                 355                 360                 365

Leu Ser Ile Asp Ser Gly Tyr Phe Ser Ala Lys Cys Tyr Pro Gly Arg
             370                 375                 380

Ser Ser Ser Gly Leu Gln Leu Ile Asn Val Thr Gln His Pro Ala Arg
385                 390                 395                 400

Ile Ala Glu Thr Pro Gly Pro Lys Thr Thr Ser Leu Lys Thr Ile Asn
                 405                 410                 415

Cys Ile Asn Leu Arg Ala Ser Val Phe Lys Glu His Arg Glu Val Glu
                 420                 425                 430

Ile Asn Val Leu Leu Pro Gln Ile Ala Val Asn Leu Ser Asn Cys His
                 435                 440                 445

Val Val Ile Lys Ser His Val Cys Asp Tyr Ser Leu Asp Thr Asp Gly
             450                 455                 460

Pro Val Arg Leu Pro His Ile Ile His Glu Gly Thr Phe Ile Pro Gly
465                 470                 475                 480

Thr Tyr Lys Ile Val Ile Asp Lys Lys Asn Lys Leu Asn Asp Arg Cys
                 485                 490                 495

Thr Leu Val Thr Asn Cys Val Ile Lys Gly Arg Glu Val Arg Lys Gly
                 500                 505                 510

Gln Ser Val Leu Arg Gln Tyr Lys Thr Glu Ile Lys Ile Gly Lys Ala
             515                 520                 525

Ser Thr Gly Ser Arg Lys Leu Leu Ser Glu Glu Pro Gly Asp Asp Cys
530                 535                 540

Ile Ser Arg Thr Gln Leu Leu Arg Thr Glu Thr Ala Glu Ile His Asp
545                 550                 555                 560

Asp Asn Tyr Gly Gly Pro Gly Asp Lys Ile Thr Ile Cys Asn Gly Ser
                 565                 570                 575

Thr Ile Val Asp Gln Arg Leu Gly Ser Glu Leu Gly Cys Tyr Thr Ile
                 580                 585                 590

Asn Arg Val Lys Ser Phe Lys Leu Cys Glu Asn Ser Ala Thr Gly Lys
                 595                 600                 605

Thr Cys Glu Ile Asp Ser Thr Pro Val Lys Cys Arg Gln Gly Phe Cys
             610                 615                 620

Leu Lys Ile Thr Gln Glu Gly Arg Gly His Val Lys Leu Ser Arg Gly
625                 630                 635                 640

Ser Glu Val Val Leu Asp Ala Cys Asp Ser Ser Cys Glu Val Met Ile
                 645                 650                 655
```

-continued

```
Pro Lys Gly Thr Gly Asp Ile Leu Val Asp Cys Ser Gly Gly Gln Gln
            660                 665                 670

His Phe Leu Lys Asp Asn Leu Ile Asp Leu Gly Cys Pro Lys Ile Pro
            675                 680                 685

Leu Leu Gly Lys Met Ala Ile Tyr Ile Cys Arg Met Ser Asn His Pro
            690                 695                 700

Lys Thr Thr Met Ala Phe Leu Phe Trp Phe Ser Phe Gly Tyr Val Ile
705                 710                 715                 720

Thr Cys Ile Phe Cys Lys Ala Leu Phe Tyr Leu Ile Ile Ile Gly
                725                 730                 735

Thr Leu Gly Lys Arg Lys Lys Gln Tyr Arg Glu Leu Lys Pro Gln Thr
            740                 745                 750

Cys Thr Ile Cys Glu Thr Ala Pro Val Asn Ala Ile Asp Ala Glu Met
            755                 760                 765

His Asp Leu Asn Cys Ser Tyr Asn Ile Cys Pro Tyr Cys Ala Ser Arg
            770                 775                 780

Leu Thr Ser Asp Gly Leu Ala Arg His Val Thr Gln Cys Pro Lys Arg
785                 790                 795                 800

Lys Glu Lys Val Glu Glu Thr Glu Leu Tyr Leu Asn Leu Glu Arg Ile
            805                 810                 815

Pro Trp Val Arg Arg Lys Leu Leu Gln Val Ser Glu Ser Thr Gly Val
            820                 825                 830

Ala Leu Lys Arg Ser Ser Trp Leu Ile Val Leu Val Leu Leu Thr
            835                 840                 845

Val Ser Leu Ser Pro Val Gln Ser Ala Pro Val Gly His Gly Lys Thr
850                 855                 860

Ile Glu Thr Tyr Gln Thr Arg Glu Gly Phe Thr Ser Ile Cys Leu Phe
865                 870                 875                 880

Met Leu Gly Ser Ile Leu Phe Ile Val Ser Cys Leu Val Lys Gly Leu
                885                 890                 895

Val Asp Ser Val Ser Asn Ser Phe Phe Pro Gly Leu Ser Val Cys Lys
            900                 905                 910

Thr Cys Ser Ile Gly Ser Ile Asn Gly Phe Glu Ile Glu Ser His Lys
            915                 920                 925

Cys Tyr Cys Ser Leu Phe Cys Cys Pro Tyr Cys Arg His Cys Ser Ala
            930                 935                 940

Asp Arg Glu Ile His Gln Leu His Leu Ser Ile Cys Lys Lys Arg Lys
945                 950                 955                 960

Thr Gly Ser Asn Val Met Leu Ala Val Cys Lys Arg Met Cys Phe Arg
                965                 970                 975

Ala Thr Glu Ala Ser Ser Asn Arg Ala Leu Leu Ile Arg Ser Ile Ile
            980                 985                 990

Asn Thr Thr Phe Val Ile Cys Ile Leu Thr Leu Ala Ile Cys Val Val
            995                 1000                1005

Ser Thr Ser Ala Val Glu Met Glu Asn Leu Pro Ala Gly Thr Trp
            1010                1015                1020

Glu Arg Glu Glu Asp Leu Thr Asn Phe Cys His Gln Glu Cys Gln
            1025                1030                1035

Val Thr Glu Thr Glu Cys Leu Cys Pro Tyr Glu Ala Leu Val Leu
            1040                1045                1050

Arg Lys Pro Leu Phe Leu Asp Ser Ile Val Lys Gly Met Lys Asn
            1055                1060                1065
```

-continued

Leu Leu Asn Ser Thr Ser Leu Glu Thr Ser Leu Ser Ile Glu Ala
1070                1075                1080

Pro Trp Gly Ala Ile Asn Val Gln Ser Thr Phe Lys Pro Thr Val
1085                1090                1095

Ser Thr Ala Asn Ile Ala Leu Ser Trp Ser Ser Val Glu His Arg
1100                1105                1110

Gly Asn Lys Ile Leu Val Thr Gly Arg Ser Glu Ser Ile Met Lys
1115                1120                1125

Leu Glu Glu Arg Thr Gly Val Ser Trp Asp Leu Gly Val Glu Asp
1130                1135                1140

Ala Ser Glu Ser Lys Leu Leu Thr Val Ser Ile Met Asp Leu Ser
1145                1150                1155

Gln Met Tyr Ser Pro Val Phe Glu Tyr Leu Ser Gly Asp Arg Gln
1160                1165                1170

Val Glu Glu Trp Pro Lys Ala Thr Cys Thr Gly Asp Cys Pro Glu
1175                1180                1185

Arg Cys Gly Cys Thr Ser Ser Thr Cys Leu His Lys Glu Trp Pro
1190                1195                1200

His Ser Arg Asn Trp Arg Cys Asn Pro Thr Trp Cys Trp Gly Val
1205                1210                1215

Gly Thr Gly Cys Thr Cys Cys Gly Val Asp Val Lys Asp Leu Phe
1220                1225                1230

Thr Asp His Met Phe Val Lys Trp Lys Val Glu Tyr Ile Lys Thr
1235                1240                1245

Glu Ala Ile Val Cys Val Glu Leu Thr Ser Gln Glu Arg Gln Cys
1250                1255                1260

Ser Leu Ile Glu Ala Gly Thr Arg Phe Asn Leu Gly Pro Val Thr
1265                1270                1275

Ile Thr Leu Ser Glu Pro Arg Asn Ile Gln Gln Lys Leu Pro Pro
1280                1285                1290

Glu Ile Ile Thr Leu His Pro Lys Ile Glu Glu Gly Phe Phe Asp
1295                1300                1305

Leu Met His Val Gln Lys Val Leu Ser Ala Ser Thr Val Cys Lys
1310                1315                1320

Leu Gln Ser Cys Thr His Gly Ile Pro Gly Asp Leu Gln Val Tyr
1325                1330                1335

His Ile Gly Asn Leu Leu Lys Gly Asp Arg Val Asn Gly His Leu
1340                1345                1350

Ile His Lys Ile Glu Pro His Phe Asn Thr Ser Trp Met Ser Trp
1355                1360                1365

Asp Gly Cys Asp Leu Asp Tyr Tyr Cys Asn Met Gly Asp Trp Pro
1370                1375                1380

Ser Cys Thr Tyr Thr Gly Val Thr Gln His Asn His Ala Ala Phe
1385                1390                1395

Val Asn Leu Leu Asn Ile Glu Thr Asp Tyr Thr Lys Thr Phe His
1400                1405                1410

Phe His Ser Lys Arg Val Thr Ala His Gly Asp Thr Pro Gln Leu
1415                1420                1425

Asp Leu Lys Ala Arg Pro Thr Tyr Gly Ala Gly Glu Ile Thr Val
1430                1435                1440

Leu Val Glu Val Ala Asp Met Glu Leu His Thr Lys Lys Val Glu
1445                1450                1455

Ile Ser Gly Leu Lys Phe Ala Ser Leu Thr Cys Thr Gly Cys Tyr

```
                     1460                1465                1470

Ala Cys Ser Ser Gly Ile Ser Cys Lys Val Arg Ile His Val Asp
    1475                1480                1485

Glu Pro Asp Glu Leu Thr Val His Val Lys Ser Ser Asp Pro Asp
1490                1495                1500

Val Val Ala Ala Ser Ser Leu Met Ala Arg Lys Leu Glu Phe Gly
1505                1510                1515

Thr Asp Ser Thr Phe Lys Ala Phe Ser Ala Met Pro Lys Thr Ser
1520                1525                1530

Leu Cys Phe Tyr Ile Val Glu Arg Glu Tyr Cys Lys Ser Cys Ser
    1535                1540                1545

Glu Glu Asp Thr Gln Lys Cys Val Asp Thr Lys Leu Glu Gln Pro
1550                1555                1560

Gln Ser Ile Leu Ile Glu His Lys Gly Thr Ile Ile Gly Lys Gln
1565                1570                1575

Asn Asp Thr Cys Thr Ala Lys Ala Ser Cys Trp Leu Glu Ser Val
1580                1585                1590

Lys Ser Phe Phe Tyr Gly Leu Lys Asn Met Leu Gly Ser Val Phe
    1595                1600                1605

Gly Asn Val Phe Ile Gly Ile Leu Leu Phe Leu Ala Pro Phe Val
1610                1615                1620

Leu Leu Ile Leu Phe Phe Met Phe Gly Trp Lys Ile Leu Phe Cys
1625                1630                1635

Phe Lys Cys Cys Arg Arg Thr Arg Gly Leu Phe Lys Tyr Arg His
    1640                1645                1650

Leu Lys Asp Asp Glu Glu Thr Gly Tyr Arg Arg Ile Ile Glu Arg
1655                1660                1665

Leu Asn Asn Lys Lys Gly Lys Asn Arg Leu Leu Asp Gly Glu Arg
1670                1675                1680

Leu Ala Asp Arg Lys Ile Ala Glu Leu Phe Ser Thr Lys Thr His
    1685                1690                1695

Ile Gly
1700

<210> SEQ ID NO 5
<211> LENGTH: 15
<212> TYPE: PRT
<213> ORGANISM: Artificial Sequence
<220> FEATURE:
<223> OTHER INFORMATION: Chemically Synthesized, Peptide 1

<400> SEQUENCE: 5

Gly Asn Gly Leu Val Asp Thr Phe Thr Asn Ser Tyr Ser Phe Cys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Chemically Synthesized, Peptide 2

<400> SEQUENCE: 6

Asp Thr Phe Thr Asn Ser Tyr Ser Phe Cys Glu Ser Val Pro Asn
1               5                   10                  15

<210> SEQ ID NO 7
<211> LENGTH: 15
```

```
<212> TYPE: PRT
<213> ORGANISM: Artificial Sequence
<220> FEATURE:
<223> OTHER INFORMATION: Chemically Synthesized, Peptide 3

<400> SEQUENCE: 7

Thr Ala Ala Leu Ser Asn Lys Val Leu Ala Glu Tyr Lys Val Pro
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Chemically Synthesized, Peptide 4

<400> SEQUENCE: 8

Asp Glu Val Asp Arg Ala Ser Ala Asp Ser Met Ile Thr Asn Leu
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Chemically Synthesized, Peptide 5

<400> SEQUENCE: 9

Ala Gln Ile Asp Thr Ala Phe Ser Ser Tyr Tyr Trp Leu Tyr Lys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Chemically Synthesized, Peptide 6

<400> SEQUENCE: 10

Lys Met Lys Lys Ala Leu Leu Ser Thr Pro Met Lys Trp Gly Lys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Chemically Synthesized, Peptide 7

<400> SEQUENCE: 11

Asp Asp Ala Ala Gln Gly Ser Gly His Thr Lys Ser Ile Leu Asn
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Chemically Synthesized, Peptide 8

<400> SEQUENCE: 12

Met Asp Ile Val Ala Ser Glu His Leu Leu His Gln Ser Leu Val
1               5                   10                  15

<210> SEQ ID NO 13
<211> LENGTH: 15
<212> TYPE: PRT
```

```
<213> ORGANISM: Artificial Sequence
<220> FEATURE:
<223> OTHER INFORMATION: Chemically Synthesized, Peptide 9

<400> SEQUENCE: 13

Ser Glu His Leu Leu His Gln Ser Leu Val Gly Lys Gln Ser Pro
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Chemically Synthesized, Peptide 10

<400> SEQUENCE: 14

Ser Pro Phe Gln Asn Ala Tyr Asn Val Lys Gly Asn Ala Thr Ser
1               5                   10                  15
```